United States Patent
Yang

(10) Patent No.: US 12,257,347 B2
(45) Date of Patent: Mar. 25, 2025

(54) PHARMACEUTICAL COMPOSITION COMPRISING META ARSENITE AND METHOD OF MANUFACTURE

(71) Applicants: KOMIPHARM INTERNATIONAL AUSTRALIA PTY LTD, Burwood (AU); PANAPHIX INC., Englewood Cliffs, NJ (US)

(72) Inventor: Yong-jin Yang, Seongnam-si (KR)

(73) Assignees: Komipharm International Australia Pty Ltd, Burwood (AU); PANAPHIX INC., Englewood Cliffs, NJ (US)

(*) Notice: Subject to any disclaimer, the term of this patent is extended or adjusted under 35 U.S.C. 154(b) by 428 days.

(21) Appl. No.: 16/982,399

(22) PCT Filed: Mar. 21, 2019

(86) PCT No.: PCT/AU2019/050249
§ 371 (c)(1),
(2) Date: Sep. 18, 2020

(87) PCT Pub. No.: WO2019/178643
PCT Pub. Date: Sep. 26, 2019

(65) Prior Publication Data
US 2021/0000746 A1    Jan. 7, 2021

(30) Foreign Application Priority Data
Mar. 22, 2018  (AU) ................................ 2018900954

(51) Int. Cl.
| *A61K 9/20* | (2006.01) |
| *A61K 9/00* | (2006.01) |
| *A61K 9/28* | (2006.01) |
| *A61K 33/36* | (2006.01) |

(52) U.S. Cl.
CPC .......... *A61K 9/2054* (2013.01); *A61K 9/0053* (2013.01); *A61K 9/2009* (2013.01); *A61K 9/2013* (2013.01); *A61K 9/2095* (2013.01); *A61K 9/2846* (2013.01); *A61K 9/2893* (2013.01); *A61K 33/36* (2013.01)

(58) Field of Classification Search
CPC .. A61K 9/2054; A61K 9/0053; A61K 9/2009; A61K 9/2013; A61K 9/2095; A61K 9/2846; A61K 9/2893; A61K 33/36; A61K 9/2018; A61K 9/2027; A61K 9/205; A61K 9/2063; A61K 9/282; A61K 9/2826; A61K 9/284; A61K 9/2866; A61K 9/2059; A61K 33/18; A61K 9/0043; A61K 9/008; A61K 9/06; A61K 47/10; A61K 9/0014; A61K 47/32; A61K 47/40; A61K 9/0073; A61K 47/36; A61P 1/04; A61P 1/18; A61P 3/10; A61P 9/00; A61P 25/00; A61P 27/02; A61P 29/00; A61P 35/02; A61P 35/04; A61P 37/00; A61P 35/00; A61P 1/00; A61P 31/04; A61P 31/00; Y02A 50/30

See application file for complete search history.

(56) References Cited

U.S. PATENT DOCUMENTS

| 5,318,973 | A  | * | 6/1994  | Kasafirek .............. A61K 38/12 |
|           |    |   |         | 514/269 |
| 6,262,086 | B1 | * | 7/2001  | Whittle .............. A61K 31/4439 |
|           |    |   |         | 514/338 |
| 7,138,137 | B2 | * | 11/2006 | Cohen .................. A61K 9/2866 |
|           |    |   |         | 424/466 |
| 8,329,221 | B2 |   | 12/2012 | Thoorens et al. |
| 8,632,818 | B2 |   | 1/2014  | Thoorens et al. |
| 8,945,505 | B2 | * | 2/2015  | Yang ...................... A61P 43/00 |
|           |    |   |         | 423/601 |
| 10,058,570 | B2 | * | 8/2018  | Hwang .................. A61P 25/00 |
| 2007/0293479 | A1 |   | 12/2007 | Osinga et al. |
| 2009/0011047 | A1 |   | 1/2009  | Rademaker |
| 2009/0061022 | A1 |   | 3/2009  | Lee |
| 2011/0070314 | A1 |   | 3/2011  | Jo et al. |
| 2011/0229527 | A1 |   | 9/2011  | Deorkar et al. |
| 2012/0045520 | A1 |   | 2/2012  | Lee |
| 2012/0251628 | A1 |   | 10/2012 | Min |
| 2013/0309319 | A1 |   | 11/2013 | Hwang et al. |
| 2016/0199411 | A1 |   | 7/2016  | Rademaker |

FOREIGN PATENT DOCUMENTS

| EP | 0543541 | * | 5/1993 | .......... A61K 31/165 |
| EP | 1721615 A1 | * | 11/2006 | ............. A61K 33/14 |
| ES | 2537063 T3 | | 6/2015 | |
| IN | 00554MU2009 | | 11/2010 | |
| JP | H11-130437 A | | 5/1999 | |
| JP | 2008-546640 A | | 12/2008 | |
| JP | 2010-518022 A | | 5/2010 | |
| JP | 2011-515481 A | | 5/2011 | |
| JP | 2013-505242 A | | 2/2013 | |
| KR | 20020083458 A | | 11/2002 | |
| WO | 2003086424 A1 | | 10/2003 | |
| WO | 2005062810 | | 7/2005 | |
| WO | 2006104292 A1 | | 10/2006 | |
| WO | 2006121280 A1 | | 11/2006 | |
| WO | 2008097824 A2 | | 8/2008 | |
| WO | 2009072779 A1 | | 6/2009 | |
| WO | 2009120697 A2 | | 10/2009 | |
| WO | 2014101986 A1 | | 7/2014 | |

OTHER PUBLICATIONS

International Application No. PCT/AU2019/050249, International Preliminary Report on Patentability mailed on Oct. 1, 2020, 9 pages.

(Continued)

*Primary Examiner* — Aradhana Sasan
(74) *Attorney, Agent, or Firm* — Kilpatrick Townsend & Stockton LLP

(57) ABSTRACT

The present application relates to pharmaceutical compositions comprising a salt of arsenous acid, such as sodium meta arsenite or potassium meta arsenite, and methods of manufacturing the pharmaceutical compositions.

27 Claims, No Drawings

(56) References Cited

OTHER PUBLICATIONS

Application No. PCT/AU2019/050249, International Search Report and Written Opinion, Mailed on Apr. 3, 2019, 17 pages.
Bashir et al. "Arsenic-Induced Cell Death in Liver and Brain of Experimental Rats", *Basic & Clinical Pharmacology & Toxicology*, 2006, 98, 6 pages.
Republic of Colombia Application No. NC2020/0012963, "Search Report", Oct. 26, 2022, 10 pages.
Japanese Application No. 2021-500320, "Office Action", Jan. 31, 2023, 12 pages.

* cited by examiner

PHARMACEUTICAL COMPOSITION COMPRISING META ARSENITE AND METHOD OF MANUFACTURE

FIELD OF THE INVENTION

The present invention relates to pharmaceutical compositions comprising the sodium or potassium salt of meta-arsenite, and methods of manufacturing the pharmaceutical compositions. The present invention also relates to a method of treatment using the pharmaceutical compositions.

BACKGROUND

Cancer is a significant health problem in the world. Although advances have been made in cancer detection and treatment, no vaccine or other universally successful preventive or therapeutic method is currently available. Management of the disease currently relies on a combination of early diagnosis and aggressive treatment, which may include one or more of a variety of therapies such as surgery, radiotherapy, chemotherapy and hormone therapy. While such therapies provide benefit to many patients, a high mortality continues to be observed for many cancers. The development of improved anti-tumour agents would facilitate cancer prevention and treatment.

Unfortunately, cancer is the leading cause of death, second only to heart disease, of both men and women. In the fight against cancer, numerous techniques have been developed and are the subject of current research directed to understanding the nature and cause of the disease and to providing methods for the control or cure thereof.

Although thousands of potential anti-cancer agents have been evaluated, the treatment of human cancer remains fraught with complications, which often present an array of suboptimal treatment choices. As such, chemotherapeutic agents, which possess little or no toxicity, which are inexpensive to obtain or manufacture, which are well tolerated by the patient, and which are easily administered would be a desirable addition to the therapeutic modalities currently available to the oncologist. Agents that will selectively sensitise malignant tissue to allow lower doses of radiation or therapy to achieve the same therapeutic effect with less damage to healthy tissues are also desirable. Similarly, agents that prevent cancer from occurring or reoccurring are also desirable.

Many chemotherapeutic drugs are currently developed for intravenous use. Oral treatment with anti-cancer agents, however, is of interest due to the benefits of easy administration, better patient compliance, and the reduction in cost and the increase in the quality of life of the patients. For example, patients will be able to undergo oral treatment as outpatients. Therefore, oral drugs for cancer treatment have a future and will play a more important role than they have done in the past.

Arsenic compounds have been used as pharmaceutical agents to treat a large variety of diseases including cancer. Inorganic arsenic compounds are highly toxic. With the rapid evolvement of medicine in the 20th century, the use of medicinal arsenic waned rapidly. Interest in arsenic compounds revived when it was shown that daily intravenous administration of arsenic trioxide ($As_2O_3$) alone caused complete responses in a large majority of patients with newly diagnosed and relapsed acute promyelocytic leukaemia. A drawback of arsenic trioxide is that it is administered intravenously daily in 1-4 hr infusion for up to 6 weeks.

When arsenic trioxide is taken orally, it binds to the chloride ions in the stomach and produces arsenic chloride ($AsCl_3$). Arsenic chloride is toxic and shows serious adverse side effects. Due to the inherent toxicity of arsenic compounds when taken orally, interest in arsenic compounds for therapy has remained low. However, it is recognised that oral formulations are easy to administer to patients, and promote better patient compliance.

Thus, there is a need for improved pharmaceutical compositions comprising arsenic compounds suitable for oral administration, for use in the treatment of diseases and conditions, such as cancer and cancer pain.

SUMMARY OF THE INVENTION

The present inventor has developed an enteric coated solid pharmaceutical composition comprising sodium meta-arsenite ($O=As-O^-Na^+$) or potassium meta-arsenite ($O=As-O^- K^+$), which is suitable for oral administration, and which passes through the stomach and commences dissolution in the small intestines (where acidity is between pH 6.5-7.5).

In a first aspect, the present invention provides a pharmaceutical composition suitable for oral administration comprising:
(a) a solid core comprising sodium meta-arsenite or potassium meta-arsenite, and one or more pharmaceutically acceptable excipients, wherein the one or more pharmaceutically acceptable excipients are selected such that oxidation of meta-arsenite to meta-arsenate is minimised;
and
(b) an enteric coating comprising an enteric polymer;
wherein the weight percentage of the enteric coating is from about 6% w/w to about 20% w/w with respect to the total weight of the pharmaceutical composition, and wherein the coating thickness is from about 6.5% to about 15% of the thickness of the pharmaceutical composition.

For example, in the above aspect, the one or more pharmaceutically acceptable excipients may be selected from a filler or diluent, a disintegrant, a glidant, a lubricant, and a binder. In some embodiments, the solid core may comprise two or more of these excipients, three or more of these excipients, four or more of these excipients, or all of these excipients. Thus, in some embodiments, the solid core comprises a filler or diluent, a disintegrant, a glidant, a lubricant, and a binder.

In a second aspect, the present invention provides a pharmaceutical composition suitable for oral administration comprising:
(a) a solid core comprising sodium meta-arsenite or potassium meta-arsenite, and the following pharmaceutically acceptable excipients:
(i) a filler or diluent in a range of from about 5 to 95% w/w,
(ii) a disintegrant in a range of from about 10 to 90% w/w,
(iii) a glidant in a range of from about 0.1 to 5% w/w,
(iv) a lubricant in a range of from about 0.1 to 5% w/w, and
(v) optionally a binder in a range of from 0 to about 30% w/w;

and (b) an enteric coating comprising an enteric polymer;

wherein the pharmaceutically acceptable excipients are selected such that oxidation of meta-arsenite to meta-arsenate is minimised, wherein the weight percentage of the enteric coating is from about 6% w/w to about 20% w/w with respect to the total weight of the pharmaceutical composition, and wherein the coating thickness is from about 6.5% to about 15% of the thickness of the pharmaceutical composition.

It will be appreciated by persons skilled in the art that some excipients have multiple functions. Where an excipient included in the pharmaceutical composition of the present invention has multiple functions, it is considered that the pharmaceutical composition includes excipients with those functions, e.g. if an excipient acts as both a binder and a disintegrant, it is understood that the pharmaceutical composition comprises a binder and a disintegrant.

Preferably, the pharmaceutically acceptable excipients in the solid core have low moisture levels or low water activity in order to minimise the possibility of oxidation of the meta-arsenite to meta-arsenate. Thus, preferably, the pharmaceutical composition of the present invention does not contain excipients with high moisture levels or high water activity.

The pharmaceutical composition may be in the form of an enteric coated tablet or an enteric coated capsule. In some embodiments, the pharmaceutical composition is an enteric coated tablet. In some embodiments, the pharmaceutical composition is an enteric coated capsule.

In a third aspect, the present invention provides a method of manufacturing the pharmaceutical composition of the first aspect, the method comprising the following steps:

(a) blending an active pharmaceutical ingredient (API) selected from sodium meta-arsenite and potassium meta-arsenite with one or more pharmaceutically acceptable excipients to form a powder blend, wherein the one or more pharmaceutically acceptable excipients are selected such that oxidation of meta-arsenite to meta-arsenate is minimised;

(b) compressing the powder blend formed in step (a) to form a solid core; and (c) coating the solid core with an enteric coating comprising an enteric polymer;

wherein the weight percentage of the enteric coating is from about 6% w/w to about 20% w/w with respect to the total weight of the pharmaceutical composition, and wherein the coating thickness is from about 6.5% to about 15% of the thickness of the pharmaceutical composition.

In a fourth aspect, the present invention provides a method of manufacturing the pharmaceutical composition of the second aspect, the method comprising the following steps:

(a) blending an active pharmaceutical ingredient (API) selected from sodium meta-arsenite and potassium meta-arsenite with the following pharmaceutically acceptable excipients to form a powder blend:

(i) a filler or diluent in a range of from about 5 to 95% w/w, (ii) a disintegrant in a range of from about 10 to 90% w/w, (iii) a glidant in a range of from about 0.1 to 5% w/w, (iv) a lubricant in a range of from about 0.1 to 5% w/w, and (v) optionally a binder in a range of from 0 to about 30% w/w;

(b) compressing the powder blend formed in step (a) to form a solid core; and (c) coating the solid core with an enteric coating comprising an enteric polymer;

wherein the pharmaceutically acceptable excipients are selected such that oxidation of meta-arsenite to meta-arsenate is minimised, wherein the weight percentage of the enteric coating is from about 6% w/w to about 20% w/w with respect to the total weight of the pharmaceutical composition, and wherein the coating thickness is from about 6.5% to about 15% of the thickness of the pharmaceutical composition.

In a fifth aspect, the present invention provides a pharmaceutical composition of the first or second aspect for use in the treatment of a disease or condition, wherein the disease or condition is selected from solid malignancy, bone metastatis, metastatic neoplastic disease, primary or metastatic lung tumour, urogenital cancers, leukemia, pain, blood cancers, metastatic cancers, cancer pain, chronic pain, inflammation, autoimmune disorders, immunological disorders, diabetic retinopathy, diabetic vasculopathy, diabetic neuralgia, symptoms associated with insulitis, and ulcerative colitis.

In a sixth aspect, the present invention provides a method for the treatment of a disease and condition in a subject, comprising orally administering to the subject a pharmaceutical composition of the first or second aspect, wherein the disease or condition is selected from solid malignancy, bone metastatis, metastatic neoplastic disease, primary or metastatic lung tumour, urogenital cancers, leukemia, pain, blood cancers, metastatic cancers, cancer pain, chronic pain, inflammation, autoimmune disorders, immunological disorders, diabetic retinopathy, diabetic vasculopathy, diabetic neuralgia, symptoms associated with insulitis, and ulcerative colitis.

In a seventh aspect, the present invention provides use of a pharmaceutical composition of the first or second aspect in the manufacture of an oral medicament for the treatment of a disease or condition, wherein the disease or condition is selected from solid malignancy, bone metastatis, metastatic neoplastic disease, primary or metastatic lung tumour, urogenital cancers, leukemia, pain, blood cancers, metastatic cancers, cancer pain, chronic pain, inflammation, autoimmune disorders, immunological disorders, diabetic retinopathy, diabetic vasculopathy, diabetic neuralgia, symptoms associated with insulitis, and ulcerative colitis.

DETAILED DESCRIPTION OF EMBODIMENTS OF THE INVENTION

Preferred embodiments of the present invention are described below by way of example only.

1. Definitions

Unless otherwise herein defined, the following terms will be understood to have the general meanings which follow. The terms referred to below have the general meanings which follow when the term is used alone and when the term is used in combination with other terms, unless otherwise indicated.

The term "composition" encompasses compositions and formulations comprising the active pharmaceutical ingredient ("API") with excipients or carriers, and also compositions and formulations with encapsulating materials as a carrier to provide a capsule in which the active pharmaceutical ingredient (with or without other carriers) is surrounded by the encapsulation carrier. In pharmaceutical compositions, the excipient or carrier is "pharmaceutically acceptable" meaning that it is not biologically or otherwise undesirable, i.e., the material may be incorporated into a pharmaceutical composition administered to a patient without causing any undesirable biological effects or interacting in a deleterious manner with any of the other components of the composition in which it is contained.

By "pharmaceutically acceptable" such as in the recitation of a "pharmaceutically acceptable salt" or a "pharmaceutically acceptable excipient or carrier" is meant herein a material that is not biologically or otherwise undesirable, i.e., the material may be incorporated into a pharmaceutical composition administered to a patient without causing any undesirable biological effects or interacting in a deleterious manner with any of the other components of the composition in which it is contained.

The term "effective amount" or "therapeutically effective amount" refers to the quantity of an active pharmaceutical ingredient that is sufficient to yield a desired therapeutic response without undue adverse side effects (such as toxicity, irritation, or allergic response) commensurate with a reasonable benefit/risk ratio when used in the manner of this invention. This amount for example could be effective in delaying the growth, delaying metastasis inhibiting angiogenesis and/or telomere and/or causing shrinkage of cancer. The specific effective amount or therapeutically effective amount will vary with such factors as the particular condition being treated, the age, body weight, general health, physical condition, gender and diet of the subject, the duration of the treatment, the nature of concurrent therapy (if any), and the severity of the particular condition.

As used herein, the term "about" means a slight variation of the value specified, preferably within 10 percent of the value specified. Nevertheless, the term "about" can mean a higher tolerance of variation depending on for instance the experimental technique used. Said variations of a specified value are understood by the skilled person and are within the context of the present invention. Further, to provide a more concise description, some of the quantitative expressions given herein are not qualified with the term "about". It is understood that, whether the term "about" is used explicitly or not, every quantity given herein is meant to refer to the actual given value, and it is also meant to refer to the approximation to such given value that would reasonably be inferred based on the ordinary skill in the art, including equivalents and approximations due to the experimental and/or measurement conditions for such given value.

Unless otherwise stated, all amounts are expressed herein as percentage by weight (% w/w).

Of course, any material used in preparing the pharmaceutical composition of the present invention should be pharmaceutically pure and substantially non-toxic in the amounts employed.

2. Chemistry of Meta-Arsenite Salts

Sodium meta-arsenite and potassium meta-arsenite can be synthesised from arsenic trioxide ($As_2O_3$). For example, sodium meta-arsenite can be synthesised by reacting arsenic trioxide ($As_2O_3$) with aqueous sodium hydroxide to form trivalent sodium meta-arsenite (top left of Scheme 1 below). The solution is cooled, the sodium meta-arsenite filtered, and the water evaporated. The sodium meta-arsenite formed is then washed with methanol to remove water, filtered under vacuum, and then dried. Potassium meta-arsenite may be prepared in a similar manner to sodium meta-arsenite using aqueous potassium hydroxide instead of aqueous sodium hydroxide.

However, a major complication of the meta-arsenite salt (salt of O=As—O⁻) is its speciation chemistry and its ability to convert to a number of different forms in solution, such as when an oral dosage form comprising sodium meta-arsenite (O=As—O⁻Na⁺) or potassium meta-arsenite (O=As—O⁻ K⁺) dissolves in the stomach. For example, sodium meta-arsenite (O=As—O⁻Na⁺) is readily soluble in strong acid, in strong base, and in neutral conditions. The forms present are dependent on the pH of the solution and sodium meta-arsenite's propensity to oxidise (Scheme 1 below). Potassium meta-arsenite behaves in a similar manner to sodium meta-arsenite. In general, neutral to alkaline conditions tend to favour the formation (or retention) of As(III) (arsenite) while acidic conditions (especially in the presence of chloride ions, such as in the stomach) tend to favour the formation of As(V) (arsenate).

Scheme 1

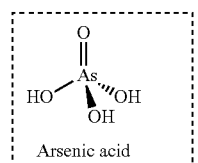

As ($^V$) Species

Arsenic acid

-continued

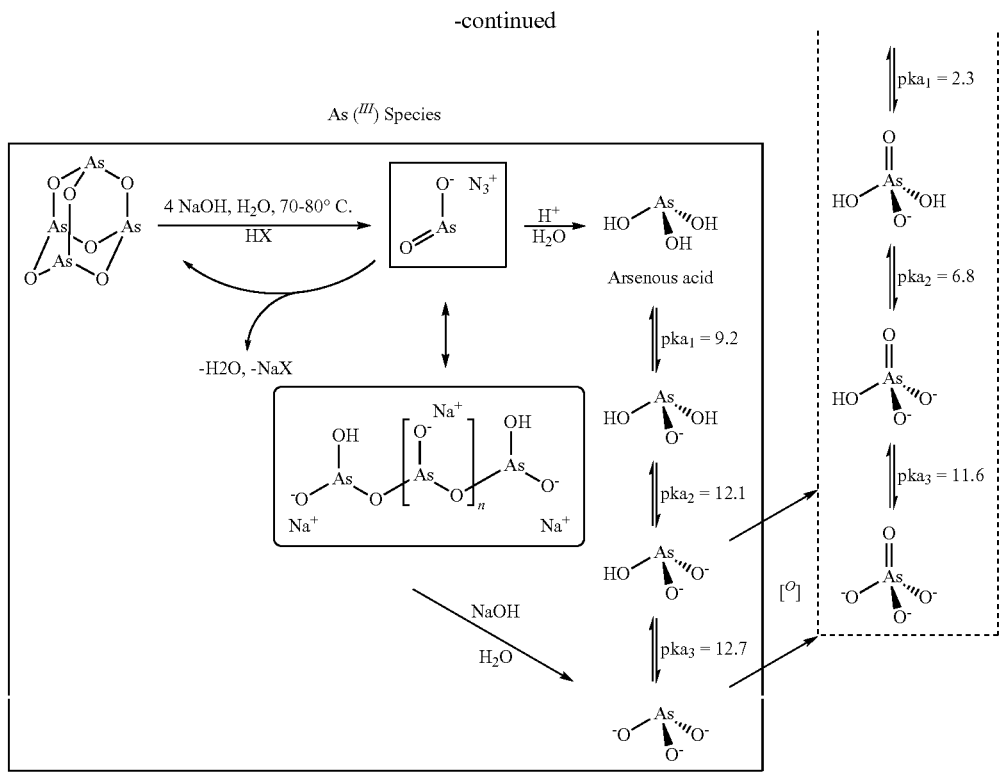

In addition, meta-arsenite ($O=As-O^-$) can oxidise to meta-arsenate during storage when chloride, metal ions or moisture (e.g. within dissolution media or within excipients; excipients may catalyse oxidation, e.g. excipients with metal ions, in particular, iron), or atmospheric oxygen, is present. Oxidation of meta-arsenite can occur quite rapidly at low pH. Sodium meta-arsenite ($O=As-O^-Na^+$) and potassium meta-arsenite ($O=As-O^-K^+$) are both hygroscopic.

In solution, the main degradant of sodium meta-arsenite is the pentavalent sodium meta-arsenate ($AsO_4^{3-}$ or As(V)) species formed by an oxidation reaction. It is hypothesised that this may proceed as shown below in Box 1, however in theory, oxidation (a change in valency) could occur without absorption of oxygen occurring (e.g. by interaction with an excipient or a reaction with metal ions present within the sodium meta-arsenite or compositions).

Box 1

| Reduced form | Oxidised form | | |
|---|---|---|---|
| $As^{3+}$ | $As^{5+} + 2e^-$ | change in As valency | (Equation 1) |
| $AsO_2^- + O_2$ | $AsO_4^{3-}$ | absorption of oxygen | (Equation 2) |

A further complication arising from the dissolution of sodium meta-arsenite ($O=As-O^-Na^+$) or potassium meta-arsenite ($O=As-O^-K^+$) in the stomach is the formation of arsenic(III) chloride ($AsCl_3$) from the chloride ions in the stomach. Oxidation of meta-arsenite may occur more rapidly when chloride is present. Arsenic(III) chloride is toxic to humans and causes serious adverse effects.

The present inventor has developed an enteric coated solid pharmaceutical composition comprising sodium meta-arsenite or potassium meta-arsenite, which is suitable for oral administration, and which passes through the stomach and commences dissolution in the small intestines (where acidity is between pH 6.5-7.5). The risk of oxidation of the meta-arsenite form to the meta-arsenate form (in the stomach or during storage), and the risk of formation of toxic arsenic(III) chloride from the chloride ions in the stomach, are minimised by employing suitable excipients and carriers, and a suitable enteric coating of a suitable thickness. The dissolution of the enteric-coated solid pharmaceutical composition in the small intestines can occur rapidly or occur over an extended period of time (e.g. 0.5, 0.75, 1, 2, 3, 4, 5 or 6 hours, preferably within 2 hours).

Preferred embodiments of the pharmaceutical composition of the present invention are described below. The pharmaceutical composition of the present invention may be manufactured through effective methods as described below.

3. Pharmaceutical Composition of the Present Invention

In a first aspect, the present invention provides a pharmaceutical composition suitable for oral administration comprising:

(a) a solid core comprising sodium meta-arsenite or potassium meta-arsenite, and one or more pharmaceutically acceptable excipients, wherein the one or more pharmaceutically acceptable excipients are selected such that oxidation of meta-arsenite to meta-arsenate is minimised;
and (b) an enteric coating comprising an enteric polymer; wherein the weight percentage of the enteric coating is from about 6% w/w to about 20% w/w with respect to the total weight of the pharmaceutical composition, and wherein the coating thickness is from about 6.5% to about 15% of the thickness of the pharmaceutical composition.

For example, in the above aspect, the one or more pharmaceutically acceptable excipients may be selected from a filler or diluent, a disintegrant, a glidant, a lubricant, and a binder. In some embodiments, the solid core may comprise two or more of these excipients, three or more of these excipients, four or more of these excipients, or all of these excipients. Thus, in some embodiments, the solid core comprises a filler or diluent, a disintegrant, a glidant, a lubricant, and a binder.

In a second aspect, the present invention provides a pharmaceutical composition suitable for oral administration comprising:
(a) a solid core comprising sodium meta-arsenite or potassium meta-arsenite, and the following pharmaceutically acceptable excipients:
(i) a filler or diluent in a range of from about 5 to 95% w/w,
(ii) a disintegrant in a range of from about 10 to 90% w/w,
(iii) a glidant in a range of from about 0.1 to 5% w/w,
(iv) a lubricant in a range of from about 0.1 to 5% w/w, and
(v) optionally a binder in a range of from 0 to about 30% w/w;
and
(b) an enteric coating comprising an enteric polymer;
wherein the pharmaceutically acceptable excipients are selected such that oxidation of meta-arsenite to meta-arsenate is minimised,
wherein the weight percentage of the enteric coating is from about 6% w/w to about 20% w/w with respect to the total weight of the pharmaceutical composition, and
wherein the coating thickness is from about 6.5% to about 15% of the thickness of the pharmaceutical composition.

The pharmaceutical composition may be in the form of an enteric coated tablet or an enteric coated capsule. In some embodiments, the pharmaceutical composition is an enteric coated tablet. In some embodiments, the pharmaceutical composition is an enteric coated capsule.

3.1 the Active Pharmaceutical Ingredient (API) (Sodium or Potassium Meta-Arsenite)

In the pharmaceutical composition of the present invention, the active pharmaceutical ingredient (API) is sodium meta-arsenite or potassium meta-arsenite.

Sodium meta-arsenite and potassium meta-arsenite can be obtained commercially in high purity (>98% As(III) and minimal levels of As(V)). Sodium meta-arsenite and potassium meta-arsenite are hygroscopic.

Being inorganic compounds, each of sodium meta-arsenite and potassium meta-arsenite has a higher particle (true) density (e.g. approximately 2.1 to 2.3 g/cm$^3$ for sodium meta-arsenite, and about 8.76 g/cm$^3$ for potassium meta-arsenite) compared with typical tablet excipients (typical tablet excipients are usually organic substances which would have a density of approximately 1.2 to 1.6 g/cm$^3$).

The potential for segregation of the API in compositions is high when there are differences in the particle size of the API and the particle size of the excipients. It will be appreciated by a person skilled in the art that using the preferred particle size of the API advantageously leads to improved powder mixing and blend uniformity, minimises or eliminates segregation in powders on compression, and achieves satisfactory content uniformity in the compositions.

In some embodiments, the particle size of the API is about 50 to 150 microns. In some embodiments, the particle size of the API is about 70 to 120 microns. In some embodiments, the particle size of the API is about 90 to 100 microns.

In some embodiments, the API is sodium meta-arsenite.
In some embodiments, the API is potassium meta-arsenite.

In some embodiments, the amount of API in the solid core of the pharmaceutical composition of the present invention is about 0.1 to 5.0% w/w of the solid core, preferably about 0.5 to 3.0% w/w of the solid core, more preferably about 1.0 to 2.5% w/w of the solid core, even more preferably about 1.5 to 2.0% w/w of the solid core, and most preferably about 1.6 to 1.8% w/w of the solid core, e.g. about 1.65% w/w, about 1.66% w/w, about 1.67% w/w, about 1.68% w/w, about 1.69% w/w, about 1.70% w/w, about 1.71% w/w, about 1.72% w/w, about 1.73% w/w, about 1.74% w/w, or about 1.75% w/w of the solid core.

In some embodiments, the particle size of the API and the particle sizes of the pharmaceutically acceptable excipients are similar. Advantageously, the use of an API and excipients with similar particle sizes can lead to improved powder mixing and blend uniformity, can minimise or eliminate segregation in powders on compression, and can achieve satisfactory content uniformity in the compositions.

In some embodiments, the API is micronised. It will be appreciated by a person skilled in the art that reducing the API particle size by micronisation may improve blend uniformity and content uniformity in dosage forms (such as tablets) when the API is present at low levels.

In some embodiments, the API is not micronised. It will be appreciated by a person skilled in the art that micronising a hygroscopic API (such as sodium meta-arsenite and potassium meta-arsenite) may lead to an increased risk of decomposition due to higher surface area and reactivity.

3.2 Pharmaceutically Acceptable Excipients

In one aspect, in addition to sodium meta-arsenite or potassium meta-arsenite, the solid core of the pharmaceutical composition of the present invention comprises one or more pharmaceutically acceptable excipients which are selected such that oxidation of meta-arsenite to meta-arsenate is minimised.

In some embodiments, the pharmaceutically acceptable excipients are selected such that less than about 10% w/w, preferably less than about 5% w/w, more preferably less than about 2% w/w, even more preferably less than about 1% w/w, and most preferably less than about 0.5% w/w of sodium meta-arsenite or potassium meta-arsenite is oxidised to sodium meta-arsenate or potassium meta-arsenate after storage at room temperature for at least about 1 month, preferably at least about 2 months, more preferably at least about 3 months, even more preferably at least about 4 months, and most preferably at least about 6 months.

In another aspect, in addition to sodium meta-arsenite or potassium meta-arsenite, the solid core of the pharmaceutical composition of the present invention comprises the following pharmaceutically acceptable excipients:
(i) a filler or diluent,
(ii) a disintegrant,
(iii) a glidant,
(iv) a lubricant, and
(v) optionally a binder.

It will be appreciated by persons skilled in the art that some excipients have multiple functions. Where an excipient included in the pharmaceutical composition of the present invention has multiple functions, it is considered that the pharmaceutical composition includes excipients with those functions, e.g. if an excipient acts as both a binder and a disintegrant, it is understood that the pharmaceutical composition comprises a binder and a disintegrant.

Generally, the one or more pharmaceutically acceptable excipients in the solid core are compatible with the sodium or potassium meta-arsenite. Preferably, the pharmaceutically acceptable excipients in the solid core have low moisture levels or low water activity in order to minimise the possibility of oxidation of the meta-arsenite to meta-arsenate. Thus, preferably, the pharmaceutical composition of the present invention does not contain excipients with high moisture levels or high water activity (such excipients may catalyse oxidation, e.g. excipients with metal ions, in particular, iron). However, it will be appreciated by persons skilled in the art that there is a limit to the practicability of this for the pharmaceutical composition of the present invention since some available moisture is necessary for satisfactory compression.

In some embodiments, the particle size of the API and the particle sizes of the pharmaceutically acceptable excipients are similar. Advantageously, the use of an API and excipients with similar particle sizes can lead to improved powder mixing and blend uniformity, can minimise or eliminate segregation in powders on compression, and can achieve satisfactory content uniformity in the solid core.

In some embodiments, where possible, higher density versions of major excipients are selected in an effort to match the density of sodium or potassium meta-arsenite (sodium meta-arsenite has an estimated true density of approximately 2.1 to 2.3 g/cm$^3$, and potassium meta-arsenite has an estimated true density of approximately 8.76 g/cm$^3$); typical tablet excipients being organic substances have a density of approximately 1.2 to 1.6 g/cm$^3$.

The filler or diluent may, for example, be selected from dibasic calcium phosphate anhydrous, partially pregelatinised starch, silicified microcrystalline cellulose, microcrystalline cellulose, calcium sulphate dihydrate, lactose, calcium hydrogen phosphate, calcium carbonate, sodium carbonate, calcium phosphate, sodium phosphate, or a mixture thereof. In some embodiments, the filler or diluent is dibasic calcium phosphate anhydrous, partially pregelatinised starch, or a mixture thereof. In some embodiments, the filler or diluent is dibasic calcium phosphate anhydrous. In some embodiments, the filler or diluent is partially pregelatinised starch. In some embodiments, the diluent may be a compressible diluent, e.g. silicified microcrystalline cellulose, microcrystalline cellulose, or partially pregelatinised starch.

The filler or diluent may be present in the solid core of the pharmaceutical composition in an amount of from about 5 to 95% w/w of the solid core. In some embodiments, the filler or diluent is present in the solid core of the pharmaceutical composition in an amount of from about 10 to 90% w/w of the solid core, e.g. about 10% w/w of the solid core, about 15% w/w of the solid core, about 20% w/w of the solid core, about 25% w/w of the solid core, about 30% w/w of the solid core, about 35% w/w of the solid core, about 40% w/w of the solid core, about 45% w/w of the solid core, about 50% w/w of the solid core, about 55% w/w of the solid core, about 60% w/w of the solid core, about 65% w/w of the solid core, about 70% w/w of the solid core, about 75% w/w of the solid core, about 80% w/w of the solid core, about 85% w/w of the solid core, or about 90% w/w of the solid core.

The disintegrant may, for example, be selected from L-hydroxypropyl cellulose, partially pregelatinised starch, crospovidone, potato starch, corn starch, sodium starch glycolate, and alginic acid. Sodium starch glycolate and crospovidone are super disintegrants. In some embodiments, the disintegrant is L-hydroxypropyl cellulose, partially pregelatinised starch, sodium starch glycolate, or a mixture of two or more thereof. In some embodiments, the disintegrant is L-hydroxypropyl cellulose. In some embodiments, the disintegrant is partially pregelatinised starch. In some embodiments, the disintegrant is sodium starch glycolate.

The disintegrant may be present in the solid core of the pharmaceutical composition in an amount of from about 10 to 90% w/w of the solid core, e.g. about 10 to 50% w/w of the solid core. In some embodiments, the disintegrant is present in the solid core of the pharmaceutical composition in an amount of from about 15 to 85% w/w of the solid core, e.g. about 15% w/w of the solid core, about 20% w/w of the solid core, about 25% w/w of the solid core, about 30% w/w of the solid core, about 35% w/w of the solid core, about 40% w/w of the solid core, about 45% w/w of the solid core, about 50% w/w of the solid core, about 55% w/w of the solid core, about 60% w/w of the solid core, about 65% w/w of the solid core, about 70% w/w of the solid core, about 75% w/w of the solid core, about 80% w/w of the solid core, or about 85% w/w of the solid core.

The glidant may, for example, be selected from colloidal silicon dioxide and talc. In some embodiments, the glidant is colloidal silicon dioxide. In some embodiments, the glidant is talc.

The glidant may be present in the solid core of the pharmaceutical composition in an amount of from about 0.1 to 5% w/w of the solid core. In some embodiments, the glidant is present in the solid core of the pharmaceutical composition in an amount of from about 0.3 to 4% w/w of the solid core, e.g. about 0.3% w/w of the solid core, about 0.4% w/w of the solid core, about 0.5% w/w of the solid core, about 0.6% w/w of the solid core, about 0.7% w/w of the solid core, about 0.8% w/w of the solid core, about 0.9% w/w of the solid core, about 1.0% w/w of the solid core, about 1.1% w/w of the solid core, about 1.2% w/w of the solid core, about 1.3% w/w of the solid core, about 1.4% w/w of the solid core, about 1.5% w/w of the solid core, about 1.6% w/w of the solid core, about 1.7% w/w of the solid core, about 1.8% w/w of the solid core, about 1.9% w/w of the solid core, about 2.0% w/w of the solid core, about 2.1% w/w of the solid core, about 2.2% w/w of the solid core, about 2.3% w/w of the solid core, about 2.4% w/w of the solid core, about 2.5% w/w of the solid core, about 2.6% w/w of the solid core, about 2.7% w/w of the solid core, about 2.8% w/w of the solid core, about 2.9% w/w of the solid core, about 3.0% w/w of the solid core, about 3.1% w/w of the solid core, about 3.2% w/w of the solid core, about 3.3% w/w of the solid core, about 3.4% w/w of the solid core, about 3.5% w/w of the solid core, about 3.6% w/w of the solid core, about 3.7% w/w of the solid core, about 3.8% w/w of the solid core, about 3.9% w/w of the solid core, or about 4.0% w/w of the solid core.

The lubricant may, for example, be selected from sodium stearyl fumarate, magnesium stearate, stearic acid, talc, and silica. In some embodiments, the lubricant is sodium stearyl fumarate. In some embodiments, the lubricant is magnesium stearate. In some embodiments, the lubricant is stearic acid. In some embodiments, the lubricant is talc. In some embodiments, the lubricant is silica.

The lubricant may be present in the solid core of the pharmaceutical composition in an amount of from about 0.1 to 5% w/w of the solid core. In some embodiments, the lubricant is present in the solid core of the pharmaceutical composition in an amount of from about 0.3 to 4% w/w of the solid core, e.g. about 0.3% w/w of the solid core, about 0.4% w/w of the solid core, about 0.5% w/w of the solid core, about 0.6% w/w of the solid core, about 0.7% w/w of the solid core, about 0.8% w/w of the solid core, about 0.9% w/w of the solid core, about 1.0% w/w of the solid core, about 1.1% w/w of the solid core, about 1.2% w/w of the solid core, about 1.3% w/w of the solid core, about 1.4% w/w of the solid core, about 1.5% w/w of the solid core, about 1.6% w/w of the solid core, about 1.7% w/w of the solid core, about 1.8% w/w of the solid core, about 1.9% w/w of the solid core, about 2.0% w/w of the solid core, about 2.1% w/w of the solid core, about 2.2% w/w of the solid core, about 2.3% w/w of the solid core, about 2.4% w/w of the solid core, about 2.5% w/w of the solid core, about 2.6% w/w of the solid core, about 2.7% w/w of the solid core, about 2.8% w/w of the solid core, about 2.9% w/w of the solid core, about 3.0% w/w of the solid core, about 3.1% w/w of the solid core, about 3.2% w/w of the solid core, about 3.3% w/w of the solid core, about 3.4% w/w of the solid core, about 3.5% w/w of the solid core, about 3.6% w/w of the solid core, about 3.7% w/w of the solid core, about 3.8% w/w of the solid core, about 3.9% w/w of the solid core, or about 4.0% w/w of the solid core.

If present, the binder may, for example, be selected from silicified microcrystalline cellulose, microcrystalline cellulose, partially pregelatinised starch, L-hydroxypropyl cellulose (low substituted hydroxypropylcellulose), hydroxypropyl cellulose, copovidone (polyvinylpyrrolidone), pregelatinised maize starch, hydroxypropylmethylcellulose, starch, acacia, corn starch, and gelatin. In some embodiments, the binder is L-hydroxypropyl cellulose (low substituted hydroxypropylcellulose). In some embodiments, the binder is a mixture of L-hydroxypropyl cellulose (low substituted hydroxypropylcellulose) and hydroxypropyl cellulose. In some embodiments, the binder is partially pregelatinised starch.

The binder may be present in the solid core of the pharmaceutical composition in an amount of from about 0 to 30% w/w of the solid core. In some embodiments, the binder is present in the solid core of the pharmaceutical composition in an amount of from about 1 to 30% w/w of the solid core, e.g. about 5 to 25% w/w of the solid core. For example, the binder may be present in the solid core of the pharmaceutical composition in an amount of about 5% w/w of the solid core, about 10% w/w of the solid core, about 15% w/w of the solid core, about 20% w/w of the solid core, about 25% w/w of the solid core, about 30% w/w of the solid core.

The pharmaceutical composition of the present invention may optionally comprise an antioxidant in the solid core. Antioxidants function as reducing agents by: (a) lowering redox potential, (b) scavenging oxygen, or (c) by terminating free radical reactions (acting as free radical inhibitors). Mechanisms (a) and (b) are most relevant to the degradation of sodium or potassium meta-arsenite to sodium or potassium meta-arsenate. Advantageously, the antioxidant acts to reduce or prevent the oxidation of As(III) to As(V) in the composition.

Examples of antioxidants that may be used in the solid core include: sodium sulphite, sodium bisulphite, sodium metabisulphite, sodium sulphate, sodium thiosulphate, cysteine hydrochloride, ascorbic acid, propyl gallate, butylated hydroxytoluene (BHT), and butylated hydroxyanisole (BHA).

The antioxidant may be present in the solid core in an amount of from about 0.01 to 0.2% w/w, e.g. 0.01% w/w, 0.02% w/w, 0.03% w/w, 0.04% w/w, 0.05% w/w, 0.06% w/w, 0.07% w/w, 0.08% w/w, 0.09% w/w, 0.10% w/w, 0.11% w/w, 0.12% w/w, 0.13% w/w, 0.14% w/w, 0.15% w/w, 0.16% w/w, 0.17% w/w, 0.18% w/w, 0.19% w/w, or 0.20% w/w of the solid core.

It will be appreciated that a person skilled in the art would understand that the amounts of the API (sodium meta-arsenite or potassium meta-arsenite), excipients and other ingredients in the solid core are adjusted to make up 100% of the solid core.

Advantageously, the solid core of the pharmaceutical composition of the present invention has good blend uniformity and content uniformity due to the use of suitable excipients as described above.

In some embodiments, the solid core of the pharmaceutical composition of the present invention does not comprise any one or more of the following: silicified microcrystalline cellulose, microcrystalline cellulose, calcium sulphate dihydrate, copovidone (polyvinylpyrrolidone), crospovidone, stearic acid, talc, and sodium metabisulphite.

3.3 Enteric Coating

The pharmaceutical composition of the present invention includes an enteric coating comprising an enteric polymer. The enteric coating may be applied by using suitable coating techniques known in the art. The enteric coating material may be dispersed or dissolved in either water or in suitable organic solvents.

As enteric coating polymers, one or more, separately or in combination, of the following may, for example, be used: solutions or dispersions of copolymers of acrylic acids and their esters or methacrylic acids or their esters, polysorbates, cellulose acetate phthalate polymers, hydroxypropyl methylcellulose phthalate polymers, hydroxypropyl methylcellulose acetate succinate, polyvinyl acetate phthalate, cellulose acetate trimellitate, carboxymethylethylcellulose, shellac, or other suitable enteric coating polymer(s).

In some embodiments, the enteric coating is a methacrylate-based coating, for example, comprising a copolymer of methacrylic acid and ethyl acrylate. Several useful products are commercially available.

Enteric coating polymer products are available from Rohm GmbH & Co., Darmstadt, Germany under the trade mark EUDRAGIT® including L100, L100-55 and S100. Examples of useful EUDRAGIT® products include EUDRAGIT L100-55, EUDRAGIT S100, and EUDRAGIT L30D-55. EUDRAGIT L100-55 is poly(methacrylic acid-co-ethyl acrylate) (1:1). EUDRAGIT S100 is methacrylic acid-methyl methacrylate copolymer (1:2). EUDRAGIT L30D-55 is an aqueous dispersion of a pH dependent polymer soluble at or above pH 5.5 for targeted delivery in the duodenum. The methacrylic acid copolymer EUDRAGIT L30D-55 is a copolymer of methacrylic acid and ethyl acrylate in a 1:1 ratio and has the formula $(C_5H_2O_2 \cdot C_4H_6O_2)_x$.

Acryl-EZE® from Colorcon is an aqueous acrylic enteric system, is dispersible in water, for the application of an enteric film coating to solid dosage forms such as tablets, granules and beads. Examples of useful Acryl-EZE® products include Acryl-EZE II white (493Z180022) and Acryl-EZE Green (93011863).

The enteric coating may further contain pharmaceutically acceptable plasticizers to obtain the desired mechanical properties, such as flexibility and hardness of the enteric coating. Such plasticizers are, for example, but not restricted to, triacetin, citric acid esters, phthalic acid esters, dibutyl sebacate, cetyl alcohol, polyethylene glycols, polysorbates or other plasticizers. Anti-tacking agents such as, for example, magnesium stearate, titanium dioxide, talc, and other additives may also be included in the enteric coating.

In some embodiments, the enteric coating provides a weight gain of about 7 to 17% w/w of the solid core, e.g. a weight gain of about 8 to 14% w/w of the solid core. In some embodiments, the enteric coating provides a weight gain of about 8% w/w, a weight gain of about 8.5% w/w, a weight gain of about 9% w/w, a weight gain of about 9.5% w/w, a weight gain of about 10% w/w, a weight gain of about 10.5% w/w, a weight gain of about 11% w/w, a weight gain of about 11.5% w/w, a weight gain of about 12% w/w, a weight gain of about 12.5% w/w, a weight gain of about 13% w/w, a weight gain of about 13.5% w/w, or a weight gain of about 14% w/w. In some embodiments, the enteric coating provides a weight gain of about 12% w/w of the solid core.

In some embodiments, the solid core may be sub-coated prior to coating with an enteric coating, using polymers known in the art for being suitable for sub-coating.

3.4 Forms of the Pharmaceutical Composition of the Present Invention

The pharmaceutical composition of the present invention is solid, enteric coated, and suitable for oral administration, e.g. enteric coated tablets or enteric coated capsules.

In some embodiments, the pharmaceutical composition of the present invention is an enteric coated tablet which has a solid core having a diameter of from about 5 to 8 mm. The diameter is the diameter of the widest dimension of the solid core. In some embodiments, the solid core diameter is about 5.5 to 7.5 mm. In some embodiments, the solid core diameter is about 6.0 to 7 mm, e.g. about 6 mm, about 6.5 mm or about 7 mm. Preferably, the pharmaceutical composition of the present invention is an enteric coated tablet which has a solid core having a diameter of 6.5 mm. More preferably, the pharmaceutical composition of the present invention is an enteric coated tablet which has a solid core having a diameter of 6.5 mm, and which comprises sodium meta-arsenite.

In some embodiments, the thickness of the solid core of the enteric coated tablet may be from about 2 mm to 6 mm, e.g. from about 2 mm to 5 mm. The thickness of the solid core of the enteric coated tablet is the depth of the solid core, i.e. the height of the solid core as measured when the solid core is resting on a flat surface. In some embodiments, the thickness of the solid core of the enteric coated tablet is about 3 to 4.5 mm. In some embodiments, the thickness of the solid core of the enteric coated tablet is about 3.1 to 4.2 mm, e.g. about 3.1 mm, about 3.2 mm, about 3.3 mm, about 3.4 mm, about 3.5 mm, about 3.6 mm, about 3.7 mm, about 3.8 mm, about 3.9 mm, about 4.0 mm, about 4.1 mm, or about 4.2 mm. Preferably, the thickness of the solid core of the enteric coated tablet is about 3.4 mm, about 3.5 mm, about 3.6 mm, about 3.7 mm, about 3.8 mm, or about 3.9 mm.

In some embodiments, the pharmaceutical composition of the present invention is an enteric coated capsule which has a solid core having a length of from about 8.0 to 16 mm. In some embodiments, the solid core length is about 8.5 to 15 mm. In some embodiments, the solid core length is about 8.5 to 14.5 mm, e.g. about 8.5 mm, about 9.0 mm, about 9.5 mm, about 10.0 mm, about 10.5 mm, about 11.0 mm, about 11.5 mm, about 12.0 mm, about 12.5 mm, about 13.0 mm, about 13.5 mm, about 14 mm, or about 14.5 mm. Preferably, the pharmaceutical composition of the present invention is an enteric coated capsule which has a solid core having a length of about 14.3 mm. More preferably, the pharmaceutical composition of the present invention is an enteric coated capsule which has a solid core having a length of about 14.3 mm, and which comprises sodium meta-arsenite.

In some embodiments, the thickness of the solid core of the enteric coated capsule may be from about 3 mm to 8 mm, e.g. from about 4.0 mm to 7.0 mm. The thickness of the solid core of the enteric coated capsule is the depth of the solid core, i.e. the height of the solid core as measured when the solid core is resting on a flat surface. In some embodiments, the thickness of the solid core is about 4.5 to 6.5 mm, e.g. about 4.5 mm, about 4.6 mm, about 4.7 mm, about 4.8 mm, about 4.9 mm, about 5.0 mm, about 5.1 mm, about 5.2 mm, about 5.3 mm, about 5.4 mm, about 5.5 mm, about 5.6 mm, about 5.7 mm, about 5.8 mm, about 5.9 mm, about 6.0 mm, about 6.1 mm, about 6.2 mm, about 6.3 mm, about 6.4 mm, or about 6.5 mm. Preferably, the thickness of the solid core of the enteric coated capsule is about 5.31 mm.

In some embodiments, the hardness of the solid core is from about 50 N to about 200 N, e.g. from about 50 to about 150 N or from about 70 to about 120 N. In some embodiments, the hardness of the solid core is from about 80 N to about 115 N, e.g. about 85 N, about 90 N, about 95 N, about 100 N, about 105 N, or about 110 N. In some embodiments, the hardness of the solid core is at least about 50 N, at least about 55 N, at least about 60 N, at least about 65 N, at least about 70 N, at least about 75 N, at least about 80 N, at least about 85 N, at least about 90 N, at least about 95 N, at least about 100 N, at least about 105 N, at least about 110 N, at least about 115 N, at least about 120 N, at least about 125 N, at least about 130 N, at least about 135 N, at least about 140 N, at least about 145 N, at least about 150 N, at least about 155 N, at least about 160 N, at least about 165 N, at least about 170 N, at least about 175 N, at least about 180 N, at least about 185 N, at least about 190 N, at least about 195 N, or about 200 N. Preferably, the hardness of the solid core is at least about 85 N, more preferably at least about 90 N, even more preferably at least about 100 N, and most preferably at least about 110 N. Typically, the hardness of the solid core does not exceed about 210 N.

In some embodiments, the friability of the solid core is less than about 0.5%, preferably less than about 0.45%, more preferably less than about 0.4%, even more preferably less than about 0.35%, and most preferably less than about 0.3%. In some embodiments, the friability of the solid core is less than about 0.25%. In some embodiments, the friability of the solid core is less than about 0.2%. In some embodiments, the friability of the solid core is less than about 0.15%. In some embodiments, the friability of the solid core is less than about 0.1%, e.g. about 0.08%.

In some embodiments, the mass of the solid core is from about 50 mg to 250 mg. In some embodiments, the mass of the solid core is from about 80 mg to 220 mg. In some embodiments, the mass of the solid core is from about 100 mg to 200 mg. In some embodiments, the mass of the solid core is from about 120 mg to 180 mg. In some embodiments, the mass of the solid core is from about 140 mg to 160 mg, e.g. about 140 mg, about 145 mg, about 150 mg, about 155 mg or about 160 mg. Preferably, the mass of the solid core is 150 mg.

In some embodiments, the pharmaceutical composition of the present invention comprises a solid core selected from the following:
 a solid core comprising sodium meta-arsenite, dibasic calcium phosphate anhydrous, L-hydroxypropyl cellulose, hydroxypropyl cellulose, colloidal silicon dioxide, and sodium stearyl fumarate;
 a solid core comprising sodium meta-arsenite, dibasic calcium phosphate anhydrous powder, partially pregelatinised starch, dibasic calcium phosphate anhydrous, sodium starch glycolate, colloidal silicon dioxide, and sodium stearyl fumarate;

a solid core comprising sodium meta-arsenite, dibasic calcium phosphate anhydrous powder, dibasic calcium phosphate anhydrous, L-hydroxypropyl cellulose, sodium starch glycolate, colloidal silicon dioxide, and sodium stearyl fumarate;

a solid core comprising sodium meta-arsenite, dibasic calcium phosphate anhydrous, partially pregelatinised starch, sodium starch glycolate, colloidal silicon dioxide, and sodium stearyl fumarate; and a solid core comprising sodium meta-arsenite, dibasic calcium phosphate anhydrous, silicified microcrystalline cellulose, sodium starch glycolate, colloidal silicon dioxide, and sodium stearyl fumarate.

In some embodiments, the pharmaceutical composition of the present invention is an enteric coated tablet comprising 1.67% w/w sodium meta-arsenite of the solid core, and having a solid core diameter of about 6.5 mm, a solid core mass of 150 mg, and an enteric coating which has added about 12% w/w of the solid core.

In some embodiments, the pharmaceutical composition of the present invention is an enteric coated tablet comprising 1.67% w/w sodium meta-arsenite of the solid core, and having a solid core diameter of about 6.5 mm, a solid core mass of 150 mg, and an enteric coating having a coating thickness of about 0.2 mm.

In some embodiments, after administration of the pharmaceutical composition of the present invention, the pharmaceutical composition has the following dissolution properties: not less than 75% in 45 minutes, preferably not less than 75% in 30 minutes.

In some embodiments, the dissolution of the pharmaceutical composition of the present invention and release of the API in the small intestines occurs rapidly or occurs over an extended period of time (e.g. 0.5, 0.75, 1, 2, 3, 4, 5 or 6 hours, preferably within 2 hours).

In some embodiments, upon dissolution of the enteric coating, the solid core disintegrates in less than about 10 minutes, preferably less than about 8 minutes, more preferably less than about 6 minutes, even more preferably less than about 5 minutes, and most preferably less than about 4 minutes.

The pharmaceutical composition of the present invention is preferably presented in unit dosage forms. The unit dosage form may be a packaged preparation, the package containing discrete quantities of the pharmaceutical composition, such as packeted tablets or capsules. Also, the unit dosage form may be a tablet or capsule itself, or it may be the appropriate number of any of these in packaged form. The packaged form may, for example, comprise metal or plastic foil, such as a blister pack, such as Alu-Alu blisters which are impermeable or less permeable to oxygen. The packaged form may be accompanied by instructions for administration.

In some embodiments, the pharmaceutical composition of the present invention may be stored at ambient or room temperature for at least three months, preferably at least six months, more preferably at least one year, and most preferably for 18-24 months. In some embodiments, the pharmaceutical composition of the present invention may be refrigerated (e.g. at about 2-8° C.).

3.5 Dosages

Suitable dosages of the sodium or potassium meta-arsenite can be readily determined by a person skilled in the art.

An appropriate dosage level of the sodium or potassium meta-arsenite administered to a subject will generally be about 0.01-0.8 mg/kg subject body weight per day, e.g. about 0.05-0.7 mg/kg subject body weight per day, about 0.1-0.6 mg/kg subject body weight per day, or about 0.2-0.5 mg/kg of subject body weight per day, which can be administered in single or multiple doses per day.

For example, an appropriate dosage level of the sodium or potassium meta-arsenite administered to a patient (e.g. a cancer patient) may be about 2.0 to 30 mg/day/person, e.g. about 2.5 to 20.0 mg/day/person or about 2.5 to 17.5 mg/day/person. Preferably, the dosage level of the sodium or potassium meta-arsenite administered is about 5.0 to 12.5 mg/day/person, more preferably about 10.0 to 12.5 mg/day/person, e.g. 5.0 mg/day/person, 5.5 mg/day/person, 6.0 mg/day/person, 6.5 mg/day/person, 7.0 mg/day/person, 7.5 mg/day/person, 8.0 mg/day/person, 8.5 mg/day/person, 9.0 mg/day/person, 9.5 mg/day/person, 10.0 mg/day/person, 10.5 mg/day/person, 11.0 mg/day/person, 11.5 mg/day/person, 12.0 mg/day/person, or 12.5 mg/day/person.

It will be understood that the specific dose level and frequency of dosage for any particular subject may be varied and will depend upon a variety of factors including the age, body weight, general health, sex and diet of the subject, the mode and time of administration, rate of excretion, drug combinations, and the severity of the particular condition.

The pharmaceutical composition of the present invention may be taken before (e.g. 30 minutes before) a meal, during a meal, or after (e.g. 30 minutes after) a meal. Preferably, the pharmaceutical composition of the present invention is taken immediately after a meal.

An example dosing regimen for a tablet of the present invention having 2.5 mg of sodium meta-arsenite (SMA) is set out below:

5.0 mg SMA intake: 1× tablet right after breakfast, 1× tablet right after dinner;

7.5 mg SMA intake: 2× tablets right after breakfast, 1× tablet right after dinner;

10.0 mg SMA intake: 2× tablets right after breakfast, 2× tablets right after dinner.

3.6 Applications

The pharmaceutical composition of the present invention is useful in clinical applications to treat various diseases and conditions.

The pharmaceutical composition of the invention may, for example, be used to treat the following diseases and conditions:

solid malignancy, such as colon tumour, gastric tumour, mammary tumour, ovarian tumour, prostate tumour, and renal tumour (solid malignancy belonging to the group consisting of colon tumour, mammary tumour, prostate tumour, and renal tumour are particularly sensitive to treatment by sodium meta-arsenite); see WO 2003/086424 which is incorporated herein by reference;

solid tumour (e.g. solid tumour of the epithelial tissue; lymphoid tissue; connective tissue; bone; or central nervous-system, such as neuroblastoma, retinoblastoma, glioblastoma or oligodendroglioma); bone metastatis; metastatic neoplastic disease (e.g. cancer of the lymphoid tissue, including Hodgkin's lymphoma, non-Hodgkin's lymphoma, follicular lymphoma, diffuse lymphoma, lymphoblastic lymphoma, large cell lymphoma or small cell lymphoma); primary or metastatic lung tumour; urogenital cancers such as cancer of the prostate, bladder, kidney and testis; leukemia (e.g. acute promyelocytic leukaemia, acute myelogenous leukaemia, and acute lymphoblastic leukaemia); see WO 2006/121280 which is incorporated herein by reference;

pain (including cancer pain and non-cancer associated pain, e.g. visceral pain, post- or peri-surgical pain, central pain, chronic pain, neuropathic pain, spinal pain, pain associated with an infectious disease, pain associated with a surgical procedure, headache, burn, angina, Herpes neuralgia, dental condition, diabetic neuropathy, fibromyalgia, NSAID-resistant condition, somatoform disorders, cystitis, muscular injury, dysmenorrhea, osteoarthritis, and stroke); inflammation (including non-cancer associated inflammation, such as that associated with asthma, pulmonary disease, autoimmune disease, arthritis, lupus erythematosus, multiple sclerosis, Crohn's disease, ulcerative colitis, chronic obstructive pulmonary, and Type I diabetes), autoimmune disorders, and immunological disorders (e.g. tissue rejection or organ rejection); diabetic retinopathy; diabetic vasculopathy; diabetic neuralgia; symptoms associated with insulitis, ulcerative colitis; see WO 2008/097824 which is incorporated herein by reference;

cancer, including cancer associated with cancer cells containing chromosomes having long telomeres (e.g. lung cancer such as non-small cell lung cancer, and prostate cancer); see WO 2009/120697 which is incorporated herein by reference;

blood cancers, metastatic cancers, cancer pain, or chronic pain.

3.7 Administration with Other Agents

In some embodiments, the pharmaceutical composition of the present invention may be used in combination with one or more other agents.

For example, the pharmaceutical composition of the present invention may be administered with other therapeutic agents, such as analgesics, anaesthetics, antianginals, antifungals, antibiotics, anti-cancer drugs (e.g., non-arsenic anti-cancer agents such as mitomycin C, cisplatin, paclitaxel and docetaxel), anti-inflammatories (e.g., ibuprofen and indomethacin), anthelmintics, antidepressants, antidotes, antiemetics, antihistamines, antihypertensives, antimalarials, antimicrotubule agents (e.g., colchicine or *vinca* alkaloids), antimigraine agents, antimicrobials, antiphsychotics, antipyretics, antiseptics, anti-signalling agents (e.g., protein kinase C inhibitors or inhibitors of intracellular calcium mobilization), antiarthritics, antithrombin agents, antituberculotics, antitussives, antivirals, appetite suppressants, cardioactive drugs, chemical dependency drugs, cathartics, chemotherapeutic agents, coronary, cerebral or peripheral vasodilators, contraceptive agents, depressants, diuretics, expectorants, growth factors, hormonal agents, hypnotics, immunosuppression agents, narcotic antagonists, parasympathomimetics, sedatives, stimulants, sympathomimetics, toxins (e.g., cholera toxin), tranquillisers and urinary anti-infectives.

It will be understood that the combined administration of the pharmaceutical composition of the present invention with the one or more other agents may be concurrent, sequential or separate administration.

4. Method of Manufacturing the Pharmaceutical Composition of the Present Invention In a third aspect, the present invention provides a method of manufacturing the pharmaceutical composition of the first aspect, the method comprising the following steps:

(a) blending an active pharmaceutical ingredient (API) selected from sodium meta-arsenite and potassium meta-arsenite with one or more pharmaceutically acceptable excipients to form a powder blend, wherein the one or more pharmaceutically acceptable excipients are selected such that oxidation of meta-arsenite to meta-arsenate is minimised;

(b) compressing the powder blend formed in step (a) to form a solid core; and (c) coating the solid core with an enteric coating comprising an enteric polymer;

wherein the weight percentage of the enteric coating is from about 6% w/w to about 20% w/w with respect to the total weight of the pharmaceutical composition, and wherein the coating thickness is from about 6.5% to about 15% of the thickness of the pharmaceutical composition.

In a fourth aspect, the present invention provides a method of manufacturing the pharmaceutical composition of the second aspect, the method comprising the following steps:

(a) blending an active pharmaceutical ingredient (API) selected from sodium meta-arsenite and potassium meta-arsenite with the following pharmaceutically acceptable excipients to form a powder blend:
  (i) a filler or diluent in a range of from about 5 to 95% w/w,
  (ii) a disintegrant in a range of from about 10 to 90% w/w,
  (iii) a glidant in a range of from about 0.1 to 5% w/w,
  (iv) a lubricant in a range of from about 0.1 to 5% w/w, and
  (v) optionally a binder in a range of from 0 to about 30% w/w;

(b) compressing the powder blend formed in step (a) to form a solid core; and (c) coating the solid core with an enteric coating comprising an enteric polymer;

wherein the pharmaceutically acceptable excipients are selected such that oxidation of meta-arsenite to meta-arsenate is minimised, wherein the weight percentage of the enteric coating is from about 6% w/w to about 20% w/w with respect to the total weight of the pharmaceutical composition, and wherein the coating thickness is from about 6.5% to about 15% of the thickness of the pharmaceutical composition.

In some embodiments of the method of the present invention, the preparation of the solid core does not involve the addition of water or solvent, i.e. no water or solvent is added during the preparation of the solid core. Thus, in some embodiments, the blending step (a) of the third and fourth aspects described above is carried out without employing water or solvent, and the compressing step (b) of the third and fourth aspects described above is carried out without employing water or solvent.

The pharmaceutical composition of the present invention may be manufactured by techniques known in the art using conventional equipment.

In general, the pharmaceutical composition of the present invention may be prepared by blending the ingredients of the composition (API and excipients) to form a blended powder. Since the concentration of API can be very low, a two- or three-stage blending process (utilising an "API premix" and a "main mix") may be utilised to improve blend uniformity. The blending times can vary depending on the ingredients. The lubricant may be added simultaneously with other ingredients in the main mix, or may be added in a later separate step to avoid possible complications from over-lubrication (e.g. reduction in tablet hardness or dissolution issues). Generally, the blending step is carried out without employing water or solvent, i.e. no water or solvent is added during the blending step. After blending, the blended powder is compressed to form a solid core. Generally, the compressing step is carried out without employing water or solvent, i.e. no water or solvent is added during the compressing step. The solid core is then coated with an enteric polymer.

Thus, in some embodiments of the method of the present invention, the blending step (step (a)) comprises two steps: the first step comprising blending the API (which has preferably been screened/sieved) with a portion of the filler (and optionally an antioxidant) to form an API premix; and the second step comprising blending the glidant (which has preferably been screened/sieved), the disintegrant, the lubricant, and optionally the binder with the API premix. In some embodiments, the blending step does not employ the use of water or solvent, i.e. no water or solvent is added during the blending step.

In some embodiments of the method of the present invention, the blending step (step (a)) comprises three steps: the first step comprising blending the API (which has preferably been screened/sieved) with a portion of the filler (and optionally an antioxidant) to form an API premix; the second step comprising blending the glidant (which has preferably been screened/sieved), the disintegrant, and optionally the binder with the API premix to form a main blend; and the third step comprising adding the lubricant (which has preferably been co-screened with a portion of the main blend) to the main blend and then blending the resulting mixture. In some embodiments, the blending step does not employ the use of water or solvent, i.e. no water or solvent is added during the blending step.

A typical preparation method utilising a three-stage blending step is described in further detail below. Typically, the three-stage blending step does not utilise water or solvent, i.e. no water or solvent is added during the three-stage blending step.

The API is firstly screened through a sieve (e.g. a hand screen). A premix containing the API (the "API premix") is prepared by blending the screened API with a portion of filler. If an antioxidant is one of the ingredients, the antioxidant may be blended into the API premix to ensure thorough mixing of the antioxidant with the API.

A glidant is screened through a sieve to de-agglomerate. Then all other ingredients including the sieved glidant, except the lubricant, is added, with the API premix sandwiched in the middle of the powder mass. The resulting mixture (the "main mix") is blended to form a blended powder (the "main blend").

The lubricant is co-screened with a small portion of the main blend, and then the co-screened mixture is added to the main blend. This lubrication step may be done separately in an effort to avoid possible complications from over-lubrication (e.g. reduction in tablet hardness or dissolution issues).

The resulting mixture is mixed thereby forming the powder blend. Following blending, the blended powder is compressed to form a solid core.

In some embodiments, the hardness of the solid core is from about 50 N to about 200 N, e.g. from about 50 to about 150 N or from about 70 to about 120 N. Typically, the targeted level of hardness is at least about 80 N, preferably at least about 85 N, more preferably at least about 90 N, and most preferably at least about 100 N. In some embodiments, the hardness of the solid core is at least about 110 N.

In some embodiments, the hardness of the solid core is from about 80 N to about 115 N, e.g. about 85 N, about 90 N, about 95 N, about 100 N, about 105 N, or about 110 N. In some embodiments, the hardness of the solid core is at least about 50 N, at least about 55 N, at least about 60 N, at least about 65 N, at least about 70 N, at least about 75 N, at least about 80 N, at least about 85 N, at least about 90 N, at least about 95 N, at least about 100 N, at least about 105 N, at least about 110 N, at least about 115 N, at least about 120 N, at least about 125 N, at least about 130 N, at least about 135 N, at least about 140 N, at least about 145 N, at least about 150 N, at least about 155 N, at least about 160 N, at least about 165 N, at least about 170 N, at least about 175 N, at least about 180 N, at least about 185 N, at least about 190 N, at least about 195 N, or about 200 N. Preferably, the hardness of the solid core is at least about 85 N, more preferably at least about 90 N, even more preferably at least about 100 N, and most preferably at least about 110 N. Typically, the hardness of the solid core does not exceed about 210 N.

The solid core may be sub-coated prior to coating with an enteric coating, using polymers known in the art for being suitable for sub-coating.

The solid core is coated with an enteric coating, for example, by spray-coating with an enteric coating dispersion. The enteric coating dispersion may be prepared, for example, by dispersing an enteric coating polymer in deionised water or an organic solvent, mixing the dispersion, and then screening through a sieve. The desired amount or thickness of the enteric coating on the solid core is achieved by standard methods known in the art, e.g. by controlling the spray rate of the enteric coating dispersion, controlling the length of time the solid cores are left in the coating pan, controlling the inlet temperature, controlling the drum speed, or atomising air pressure.

EXAMPLES

The present invention is further described below by reference to the following non-limiting Examples.

Materials and Methods

All materials used to manufacture the pharmaceutical compositions exemplified below were purchased from commercial sources.

Sodium meta-arsenite ("SMA") was obtained from Sigma Aldrich Fine Chemicals. As supplied, the SMA drug substance exhibited very high purity (>98% As(III)) and minimal levels of As(V). Table 1 below provides the properties of the supplied SMA drug substance.

TABLE 1

Properties of the supplied SMA drug substance

| Property | Value/Observation |
|---|---|
| Appearance | White to off-white powder |
| Melting point | 615° C. |
| Solubility | Approx. 950 mg/mL |
| Typical assay (As(III)) | 98-99% |
| Typical Impurity Level (As(V)) | ≤0.2% |
| Typical water content | <1.0% |
| Hygroscopicity (moisture uptake) | ~40% at 75% RH |
| | >80% at 80% RH |
| | >130% at 90% RH |
| Density (true/particle) | 2.1-2.3 g/cm$^3$ |

The materials listed in Table 2 below were used to prepare the 2.5 mg sodium meta-arsenite ("SMA") enteric coated tablets. Where possible, higher density versions of major excipients were selected in an effort to match the density of SMA (an inorganic material with an estimated true density of approximately 2.1 to 2.3 g/cm$^{-3}$, which is very dense compared with most excipients).

TABLE 2

List of materials

| Materials | Function | Trade Name/Supplier |
|---|---|---|
| Sodium meta-arsenite ("SMA") (>98% pure) | active pharmaceutical ingredient | Sigma Aldrich Fine Chemicals (Madison, Wisconsin, USA) |
| Calcium sulphate dihydrate | filler | Compactrol/JRS pharma |
| Calcium carbonate | filler | PressCAL MD 92.5/JRS |
| Calcium carbonate finer grade | filler | Not applicable/JRS |
| Dibasic calcium phosphate anhydrous | filler | Fujicalin/Fuji chemicals |
| Dibasic calcium phosphate anhydrous powder | filler | A Comprez/JRS pharma |
| Dibasic calcium phosphate anhydrous fine grade | filler | A-Comprez/JRS pharma |
| Silicified microcrystalline cellulose (sMCC) high density grade | filler, compressible diluent | Prosolv HD 90 |
| Microcrystalline cellulose (MCC) high density grade | binder | Avicel PH302/FMC |
| Partially pregelatinised starch | binder, disintegrant, filler | Lycatab C-LM/Roquette |
| Partially pregelatinised starch | binder, disintegrant, filler | Starch 1500/Colorcon |
| Hydroxypropyl cellulose | binder | Klucel EXF/Ashland |
| L-Hydroxypropyl cellulose | binder, disintegrant | LH-B1/Shin-EtSu |
| Colloidal silicon dioxide | glidant | Aerosil 200/Evonik |
| Sodium starch glycolate | super disintegrant | Explotab/JRS Pharma |
| Croscarmellose sodium | super disintegrant | Ac-di-Sol/FMC |
| Sodium stearyl fumarate | lubricant | PRUV/JRS pharma |
| Opadry II (20A280013) | sub-coat | Colorcon |
| Acryl-EZE II white (493Z180022) | coating polymer | Colorcon |

The equipment listed in Table 3 below was used in the preparation and analysis of the SMA enteric coated compositions.

TABLE 3

List of equipment

| Equipment Name | Manufacturer | Usage |
|---|---|---|
| Balance | Sartorius | weighing materials and tablets |
| Turbula blender | Turbula | blending |
| 2 L Turbula mixing jar | Turbula | blending |
| Density meter | Copley | density measurement |
| Manesty F3 press (single punch) | Manesty | tabletting |
| Rotary press (7 stations) | SCI | tabletting |
| 6.5 mm round normal biconcave NCCP tools | Natoli | tabletting |
| 0.25 inch tooling | Key International | tabletting |
| Key International tablet machine | | |
| Hardness tester | Copley | measuring tablet hardness |
| Micrometer | Mitsuyi | measuring tablet thickness |
| Friability tester | Copley | testing friability |
| Disintegration bath | Copley | testing disintegration |
| 15" Coating pan | Thai Coater | coating |

Manufacturing Example 1

The enteric coated tablets of Formulation Examples 1.1 to 1.4 comprising sodium meta-arsenite ("SMA") as the active pharmaceutical ingredient (API) were prepared following the procedure described below.

In general, and as described in detail below, the sodium meta-arsenite ("SMA") and excipients were blended together (in a three-stage blending process without the use of water or solvent) to form a powder blend. The powder blend was then compressed to form the solid core of the tablet. The solid core of the tablet was then coated with an enteric coating.

Blending

The blending process described below was used for blending the ingredients.

The API and the other ingredients for the composition were dispensed and weighed. Since the concentration of the API was very low, a three-stage blending process (utilising an "API premix" and a "main mix") was utilised in an effort to improve blend uniformity.

The API was screened through a 200 μm sieve (hand screen). The sieving time was between 5-8 minutes.

A premix containing the API (the "API premix") was prepared by blending the screened API with a few grams (20 g for a 500 g batch size and 30 g for a 700 g batch size) of filler in an appropriate container (100 ml container for a 500 g batch size and 150 ml for a 700 g batch size) for 10 minutes at 49 rpm with a Turbula blender.

The glidant (colloidal silicon dioxide) was screened through a 500 μm sieve to de-agglomerate. Then all other dispensed ingredients including the sieved glidant, except the lubricant (sodium stearyl fumarate), were added into a 2 L glass Turbula jar, with the API premix sandwiched in the middle of the powder mass.

The resulting mixture (the "main mix") was blended for between about 10 to about 20 minutes at 49 rpm using a Turbula blender to form a blended powder (the "main blend").

The lubricant (sodium stearyl fumarate) was co-screened with a small portion of the main blend using a 500 μm sieve, and then the co-screened mixture was added to the main blend. This lubrication step was done separately in an effort to avoid possible complications from over-lubrication (e.g. reduction in tablet hardness or dissolution issues).

The resulting mixture was mixed for 2 minutes at 49 rpm in the Turbula blender thereby forming the powder blend. The powder blend was characterized for flow properties.

Compressing

The powder blend was compressed on a Manesty F3 single punch tablet press using 6.5 mm normal concave plain (NCCP) tooling at a target tablet weight of 150 mg. The Manesty F3 only has arbitrary units (AU) for compression force and it is not possible to directly measure the applied force. The targeted level of hardness was above 90 N.

Enteric Coating

A 20% w/w solid content enteric coating dispersion was prepared by dispersing Acryl-EZE II white (493Z180022) in deionised water. The dispersion was stirred using a paddle stirrer for 45 minutes before use and throughout the coating process. The dispersion was screened through a 250 μm sieve before being used.

The 15" coating pan (Thai Coater) was allowed to equilibrate to the set point temperature prior to charging with the solid cores of the tablets. Due to the small batch sizes, 'bulking inerts' were added to the API solid cores to meet the loading requirements for the coating pan. The solid cores of the tablets were allowed to equilibrate in the drying pan for 10 minutes prior to coating. The same temperature and airflow was used for the heating, coating and drying phases. The coated tablets were dried for 10 minutes in the pan after coating. Samples were collected after 8, 10 and 12% w/w weight gain.

Dissolution Studies

Dissolution studies were carried out using 500 mL of media and USP Method 2 (paddles) initially with a paddle speed of 100 rpm. A single set of six enteric coated tablets (n=6) were examined. Samples of dissolution media were withdrawn after 2 hours in acid and the levels of sodium meta-arsenite determined to assess gastric resistance. The media was replaced with the pH 6.8 phosphate buffer and samples were withdrawn at intervals of 15 minutes to generate dissolution profiles.

This method is based on the pharmacopoeial method for enteric dosage forms (EP.2.9.3 and USP <711>) as shown in Table 4 below.

TABLE 4

Conditions of dissolution studies

| Stage | Conditions | Description | Purpose | Requirement |
|---|---|---|---|---|
| 1 | 0.01M HCl | Acid phase | Acid resistance | Not more than 10% release in 2 hours |
| 2 | pH 6.8 phosphate buffer | Buffer Phase | Release profile | Typically, not less than 75% in 30-45 minutes |

Formulation Example 1.1

A solid pharmaceutical composition (P63) comprising sodium meta-arsenite (SMA) as the active pharmaceutical ingredient (API) was prepared using the method described above in Manufacturing Example 1.

The composition was manufactured at a 700 g scale. Blend uniformity and content uniformity samples were collected to assess the homogeneity after the main blending time of 20 minutes.

Table 5 below provides the composition of the solid core of the tablet comprising 2.53 mg of sodium meta-arsenite (prior to the coating step). (Table 5.1 below provides another possible composition of the solid core of the tablet comprising 2.50 mg of sodium meta-arsenite (prior to the coating step).)

TABLE 5

Composition of the solid core of the P63 tablet

| Material | Function | mg/tablet | % w/w |
|---|---|---|---|
| Sodium meta-arsenite | API | 2.53 | 1.69 |
| Dibasic calcium phosphate anhydrous (A-Comprez fine granule) | filler | 82.22 | 54.81 |
| L-Hydroxypropyl cellulose (LH-B1 grade) | binder, disintegrant | 60.00 | 40.00 |
| Hydroxypropyl cellulose (Klucel EXF) | binder | 3.00 | 2.00 |
| Colloidal silicon dioxide (Aerosil 200) | glidant | 0.75 | 0.50 |
| Sodium stearyl fumarate (PRUV) | lubricant | 1.50 | 1.00 |
| Total | | 150.00 | 100.00 |

Following the blending step, the powder blend demonstrated good flow properties as indicated by the Carr's Index (29.3%). The powder blend prior to compression had the following properties:

Aerated density: 0.64 g/cm$^3$
Tapped density: 0.91 g/cm$^3$
Carr's index: 29.3%
Hausner ratio: 1.30

The powder blend compressed very well and no weight variation and/or visual segregation was observed throughout the run. High tablet hardness (104.8 N) and low friability (0.08%) were achieved, and disintegration time (34 seconds) was relatively rapid. The mean thickness of the solid core of the tablet was 3.63 mm.

Blend uniformity samples were taken after blending for 20 minutes and content uniformity samples were collected at the start, middle and end of the compression run. Blend uniformity results exhibited excellent homogeneity with a % relative standard deviation (RSD) value of 1.3. The content uniformity of the solid cores of the tablet across the compression run (start, middle and end) showed good homogeneity as a maximum acceptance value (AV) value of <7.4 was achieved (AV value of <15 is acceptable).

Following the compression step, the solid core of the tablet was coated with Acryl-EZE II white (493Z180022) enteric coating polymer system, which was prepared as described in Manufacturing Example 1. The coating parameters are shown in Table 6 below.

TABLE 6

Coating parameters

| Parameter | Result |
|---|---|
| Coating pan | 15" Thai Coater |
| Inlet Temp | 90-110° C. |
| Exhaust Temp | ~50° C. |
| Drum Speed | 16 rpm |
| Spray Rate | 10-11 g/min |
| Bed Temp | ~35° C. |
| Inlet and Exhaust Shut | Both at middle |
| Gun to Bed Distance | 5 cm (Baffles not visible) |
| Fluid nozzle (mm) | 1.2 mm |
| Fan Air Pressure | 20 psi |
| Spray gun Air Pressure | 10 psi |

TABLE 6-continued

Coating parameters

| Parameter | Result |
|---|---|
| Weight of Bulking inert (g) | 2500.0 g |
| Weight of active tablets (g) | 473.0 g |
| Weight of tablet bed (g) | 2973.0 g |
| Initial weight of 20 tablets (g) | 3.017 g |
| Target weight gain for 12% coating (g) | 3.379 g |
| Weight of 20 tablets after 12% weight gain (g) | 3.381 g |
| | (12.06% weight gain) |

The enteric coated tablet exhibited an acceptable dissolution profile (500 ml media, paddle speed 100 rpm). After 120 minutes, the composition was intact in acidic media (pH 1.0) with 0% API release. After 135 minutes at pH 6.8, 91% of the API was released. After 150 minutes at pH 6.8, 98% of the API was released. After 165 minutes at pH 6.8, 100% of the API was released.

The enteric coated tablet demonstrated satisfactory gastric resistance and met the proposed preliminary specification of not less than 75% release in 45 minutes for enteric dosage forms.

Table 5.1 below provides another possible composition of the solid core of the tablet comprising 2.50 mg of sodium meta-arsenite (prior to the coating step). A solid core having the components described in Table 5.1 may be prepared in a similar manner as described above for the solid core having the components described in Table 5.

TABLE 5.1

Alternative composition of the solid core of the P63 tablet

| Material | Function | mg/tablet | % w/w |
|---|---|---|---|
| Sodium meta-arsenite | API | 2.50 | 1.67 |
| Dibasic calcium phosphate anhydrous (A-Comprez fine granule) | filler | 82.25 | 54.83 |
| L-Hydroxypropyl cellulose (LH-B1 grade) | binder, disintegrant | 60.00 | 40.00 |
| Hydroxypropyl cellulose (Klucel EXF) | binder | 3.00 | 2.00 |
| Colloidal silicon dioxide (Aerosil 200) | glidant | 0.75 | 0.50 |
| Sodium stearyl fumarate (PRUV) | lubricant | 1.50 | 1.00 |
| Total | | 150.00 | 100.00 |

Formulation Example 1.2

A solid pharmaceutical composition (P23) comprising sodium meta-arsenite (SMA) as the active pharmaceutical ingredient (API) was prepared using the method described above in Manufacturing Example 1.

The composition was manufactured at a 500 g scale. Blend uniformity samples were collected after 10, 15 and 20 minutes of the main blending time. The blend was compressed to form the solid core of the tablet, and then the solid core of the tablet was coated.

Table 7 below provides the composition of the solid core of the tablet comprising 2.50 mg of sodium meta-arsenite (prior to the coating step).

TABLE 7

Composition of the solid core of the P23 tablet

| Material | Function | mg/tablet | % w/w |
|---|---|---|---|
| Sodium meta-arsenite | API | 2.50 | 1.67 |
| Dibasic calcium phosphate anhydrous powder (A-Comprez powder) | filler | 37.50 | 25.00 |
| Partially pregelatinised starch (Starch 1500) | binder, disintegrant, filler | 45.00 | 30.00 |
| Dibasic calcium phosphate anhydrous granule (Fujicalin) | filler | 58.25 | 38.83 |
| Sodium starch glycolate (Explotab) | Super disintegrant | 4.50 | 3.00 |
| Colloidal silicon dioxide (Aerosil 200) | glidant | 0.75 | 0.50 |
| Sodium stearyl fumarate (PRUV) | lubricant | 1.50 | 1.00 |
| Total | | 150.00 | 100.00 |

Following the blending step, the powder blend demonstrated good flow properties as indicated by the Carr's Index (26.37%). The powder blend prior to compression had the following properties:

Aerated density: 0.67 g/cm$^3$
Tapped density: 0.91 g/cm$^3$
Carr's index: 26.37%
Hausner ratio: 1.36
Angle of repose: 24.32°

Blend uniformity samples were collected after blending for 10, 15 and 20 minutes of the main blending time. The composition exhibited good homogeneity at 20 minutes blend time.

Compression was performed on a Manesty F3 single punch machine using 6.5 mm NCCP tools. The mean solid core hardness was 94.3 N, the mean thickness was 3.62 mm, the friability was 0.33%, and the disintegration time was 39 seconds.

The weight of the solid cores was consistent throughout the compression run and acceptable solid cores were produced. No visual segregation was observed. Samples (10 solid cores in duplicate) were collected at start, middle and end of the compression run and sent for content uniformity testing.

Following the compression step, the solid core of the tablet was coated with Acryl-EZE II white (493Z180022) enteric coating polymer system, which was prepared as described in Manufacturing Example 1, and samples were collected after 8, 10 and 12% w/w weight gain. The coating parameters are shown in Table 8 below.

TABLE 8

Coating parameters

| Parameter | Result |
|---|---|
| Coating Pan | Thai Coater |
| Inlet Temp | 81-90° C. |
| Exhaust Temp | ~50° C. |
| Drum Speed | 18 rpm reduced to 16 rpm |
| Initial Spray Rate | 7 g/min |
| Spray Rate after 30 minutes | 11 g/min |
| Bed Temp | ~35° C. |
| Inlet and exhaust Shut | Both at middle |
| Gun to Bed Distance | 5 cm (Baffles not visible) |
| Pump Speed | 05 |
| Fluid nozzle (mm) | 1.2 mm |
| Spray gun air pressure | 10 psi |
| Fan air pressure | 20 psi |

TABLE 8-continued

Coating parameters

| Parameter | Result |
|---|---|
| Weight of Bulking inert (g) | 3000 g |
| Weight of active tablets (g) | 240 g |
| Weight of tablet bed (g) | 3240 g |
| Initial weight of 20 tablets (g) | 3.015 g |
| % w/w target for tablet coat | 8% |
| Target weight gain for 8% coating (g) | 3.256 g |
| Amount of dispersion sprayed to achieve 8% weight gain (g) | 1900 g |
| Weight of 20 tablets after 8% weight gain (g) | 3.248 g |
| % w/w target for tablet coat | 10% |
| Target weight gain for 10% coating (g) | 3.317 g |
| Amount of dispersion sprayed to achieve 10% weight gain (g) | 2400 g |
| Weight of 20 tablets after 10% weight gain (g) | 3.328 g |
| % w/w target for tablet coat | 12% |
| Target weight gain for 12% coating (g) | 3.377 g |
| Amount of dispersion sprayed to achieve 12% weight gain (g) | 2900 g |
| Weight of 20 tablets after 12% weight gain (g) | 3.384 g |

The enteric coated tablets with weight gains of 8%, 10% and 12% w/w underwent dissolution testing (500 ml dissolution media, paddle speed 75 rpm) to identify suitable levels of enteric coating. The dissolution results are presented in Table 9 below.

TABLE 9

Dissolution results

| | Sample name Mean (% drug released) | | | | |
|---|---|---|---|---|---|
| | Time (min) | | | | |
| | 120 | 135 | 150 | 165 | 195 |
| | Media | | | | |
| | pH 1.0 | pH 6.8 | pH 6.8 | pH 6.8 | pH 6.8 |
| 8% w/w enteric coated tablets | 00 | 67 | 80.5 | 87 | 90 |
| 10% w/w enteric coated tablets | 00 | 26 | 82 | 89 | Not determined |
| 12% w/w enteric coated tablets | 00 | 27 | 83 | 90 | 92 |

The enteric coated tablets were intact in the acidic media after 120 minutes. The enteric coated tablets demonstrated satisfactory gastric resistance and met the proposed preliminary specification of not less than 75% release in 45 minutes for enteric dosage forms.

Based on the dissolution results, it was found that 12% w/w was the optimum coating weight gain.

Formulation Example 1.3

A solid pharmaceutical composition (P31) comprising sodium meta-arsenite (SMA) as the active pharmaceutical ingredient (API) was prepared using the method described above in Manufacturing Example 1.

The composition was manufactured at a 500 g scale. Blend uniformity samples were collected after 10, 15 and 20 minutes of the main blending time. The blend was compressed to form the solid core of the tablet, and then the solid core of the tablet was coated. L-Hydroxypropyl cellulose (L-HPC; low substituted hydroxypropyl cellulose LH-B1 grade) was used as it acts as a binder and disintegrant. As L-HPC is insoluble in water it was expected that this would give hard tablets.

Table 10 below provides the composition of the solid core of the tablet comprising 2.50 mg of sodium meta-arsenite (prior to the coating step).

TABLE 10

Composition of the solid core of the P31 tablet

| Material | Function | mg/tablet | % w/w |
|---|---|---|---|
| Sodium meta-arsenite | API | 2.50 | 1.67 |
| Dibasic calcium phosphate anhydrous powder (A-Comprez powder) | filler | 37.50 | 25.00 |
| Dibasic calcium phosphate anhydrous granule (Fujicalin) | filler | 80.75 | 53.83 |
| L-Hydroxypropyl cellulose (LH-B1 grade) | binder, disintegrant | 22.50 | 15.00 |
| Sodium starch glycolate (Explotab) | super disintegrant | 4.50 | 3.00 |
| Colloidal silicon dioxide (Aerosil 200) | glidant | 0.75 | 0.50 |
| Sodium stearyl fumarate (PRUV) | lubricant | 1.50 | 1.00 |
| Total | | 150.00 | 100.00 |

Following the blending step, the powder blend demonstrated good flow properties as indicated by the Carr's Index (23.68%). The powder blend prior to compression had the following properties:

Aerated density: 0.58 g/cm$^3$
Tapped density: 0.76 g/cm$^3$
Carr's index: 23.68%
Hausner ratio: 1.31
Angle of repose: 27.96°

Blend uniformity samples were collected after blending for 10, 15 and 20 minutes of the main blending time. The composition exhibited good homogeneity at 20 minutes blend time.

Compression was performed on a Manesty F3 single punch machine using 6.5 mm NCCP tools. The mean solid core hardness was 104.3 N, the mean thickness was 3.52 mm, the friability was 0.23%, and the disintegration time was 30 seconds.

The weight of the solid cores was consistent throughout the compression run and acceptable solid cores were produced. No visual segregation was observed. Samples (10 solid cores in duplicate) were collected at start, middle and end of the compression run and sent for content uniformity testing.

Following the compression step, the solid core of the tablet was coated with Acryl-EZE II white (493Z180022) enteric coating polymer system, which was prepared as described in Manufacturing Example 1, and samples were collected after 8, 10 and 12% w/w weight gain. The coating parameters are shown in Table 11 below.

TABLE 11

Coating parameters

| Coating Pan | Thai Coater |
|---|---|
| Inlet Temp | 81-90° C. |
| Exhaust Temp | 50° C. |
| Drum Speed | 18 rpm reduced to 16 rpm |
| Initial Spray Rate | 7 g/min |
| Spray Rate after 30 minutes | 11 g/min |

TABLE 11-continued

Coating parameters

| Coating Pan | Thai Coater |
|---|---|
| Bed Temp | 35° C. |
| Inlet and exhaust Shut | Both at middle |
| Gun to Bed Distance | 5 cm |
|  | (Baffles not visible) |
| Pump Speed | 05 |
| Fluid nozzle (mm) | 1.2 mm |
| Spray gun air Pressure | 10 psi |
| Fan air Pressure | 20 psi |
| Weight of Bulking inert(g) | 3000 g |
| Weight of active tablets (g) | 260 g |
| Weight of tablet bed (g) | 3260 g |
| Initial weight of 20 tablets (g) | 2.995 g |
| % w/w target for tablet coat | 8% |
| Target weight gain for 8% coating (g) | 3.235 g |
| Amount of dispersion sprayed to achieve 8% weight gain (g) | 1900 g |
| Weight of 20 tablets after 8% weight gain (g) | 3.231 g |
| % w/w target for tablet coat | 10% |
| Target weight gain for 10% coating (g) | 3.295 g |
| Amount of dispersion sprayed to achieve 10% weight gain (g) | 2400 g |
| Weight of 20 tablets after 10% weight gain (g) | 3.282 g |
| % w/w target for tablet coat | 12% |
| Target weight gain for 12% coating (g) | 3.354 g |
| Amount of dispersion sprayed to achieve 12% weight gain (g) | 2900 g |
| Weight of 20 tablets after 12% weight gain (g) | 3.362 g |

The enteric coated tablets with weight gains of 8%, 10% and 12% w/w underwent dissolution testing (500 ml dissolution media, paddle speed 75 rpm) to identify suitable levels of enteric coating. The dissolution results are presented in Table 12 below.

TABLE 12

Dissolution results

| Sample name | Mean (% drug released) | | | | |
|---|---|---|---|---|---|
|  | Time (min) | | | | |
|  | 120 | 135 | 150 | 165 | 195 |
|  |  |  | Media |  |  |
|  | pH 1.0 | pH 6.8 | pH 6.8 | pH 6.8 | pH 6.8 |
| 8% w/w enteric coated tablets | 19.6 | 0* | 0* | 0* | 0* |
| 10% w/w enteric coated tablets | 00 | 55 | 74 | 86 | not determined |
| 12% w/w enteric coated tablets | 00 | 67 | 81 | 88 | 91 |

*All tablets ruptured in acid. 0% drug dissolved in pH 6.8 media as the ruptured tablets would lead to degradation in the acid stage and therefore the API was not detected in the buffer stage.

The 8% w/w weight gain enteric coated tablets failed the acid resistance test. The 10% w/w weight gain enteric coated tablets and 12% w/w weight gain enteric coated tablets demonstrated satisfactory gastric resistance and met the proposed preliminary specification of not less than 75% release in 45 minutes for enteric dosage forms.

Based on the dissolution results, it was found that 12% w/w was the optimum coating weight gain.

Formulation Example 1.4

A solid pharmaceutical composition (P66) comprising sodium meta-arsenite (SMA) as the active pharmaceutical ingredient (API) was prepared using the method described above in Manufacturing Example 1.

The composition was manufactured at a 700 g scale. Blend uniformity and content uniformity samples were collected to assess the homogeneity after the main blending time of 20 minutes.

Table 13 below provides the composition of the solid core of the tablet comprising 2.53 mg of sodium meta-arsenite (prior to the coating step).

TABLE 13

Composition of the solid core of the P66 tablet

| Material | Function | mg/tablet | % w/w |
|---|---|---|---|
| Sodium meta-arsenite | API | 2.53 | 1.69 |
| Dibasic calcium phosphate anhydrous (A-Comprez fine granule) | filler | 71.55 | 47.70 |
| Partially pregelatinised starch (Starch 1500) | binder, disintegrant, filler | 67.67 | 45.11 |
| Sodium starch glycolate (Explotab) | super disintegrant | 6.00 | 4.00 |
| Colloidal silicon dioxide (Aerosil 200) | glidant | 0.75 | 0.50 |
| Sodium stearyl fumarate (PRUV) | lubricant | 1.50 | 1.00 |
| Total |  | 150.00 | 100.00 |

Following the blending step, the powder blend demonstrated good flow properties as indicated by the Carr's Index (25.74%). The powder blend prior to compression had the following properties:

Aerated density: 0.75 g/cm$^3$

Tapped density: 1.01 g/cm$^3$

Carr's index: 25.74%

Hausner ratio: 1.35

The powder blend compressed very well and no weight variation and/or visual segregation was observed throughout the run. High solid core hardness (87.4 N) and low friability (0.11%) were achieved, and disintegration time (2 minutes 52 seconds) was relatively rapid. The mean thickness of the solid core was 3.66 mm.

Blend uniformity samples were taken after blending for 20 minutes and content uniformity samples were collected at the start, middle and end of the compression run. Blend uniformity results exhibited excellent homogeneity with a % relative standard deviation (RSD) value of 2.1. The content uniformity of the solid cores across the compression run (start, middle and end) showed good homogeneity as a maximum acceptance value (AV) value of <6.3 was achieved (AV value of <15 is acceptable).

Following the compression step, the solid core of the tablet was coated with Acryl-EZE II white (493Z180022) enteric coating polymer system, which was prepared as described in Manufacturing Example 1. The coating parameters are shown in Table 14 below.

TABLE 14

Coating parameters

| Parameter | Result |
|---|---|
| Coating pan | 15" Thai Coater |
| Inlet Temp | 90-110° C. |
| Exhaust Temp | ~50° C. |
| Drum Speed | 16 rpm |
| Spray Rate | 10-11 g/min |
| Bed Temp | ~35° C. |
| Inlet and Exhaust Shut | Both at middle |
| Gun to Bed Distance | 5 cm (Baffles not visible) |
| Fluid nozzle (mm) | 1.2 mm |
| Fan Air Pressure | 20 psi |
| Spray gun Air Pressure | 10 psi |
| Weight of Bulking inert (g) | 2600.0 g |
| Weight of active tablets (g) | 350.0 g |
| Weight of tablet bed (g) | 2950.0 g |
| Initial weight of 20 tablets (g) | 3.010 g |
| Target weight gain for 12% coating (g) | 3.371 g |
| Weight of 20 tablets after 12% weight gain (g) | 3.380 g (12.2% weight gain) |

The enteric coated tablet exhibited an acceptable dissolution profile (500 ml media, paddle speed 100 rpm). After 120 minutes, the composition was intact in acidic media (pH 1.0) with 0% API release. After 135 minutes at pH 6.8, 21% of the API was released. After 150 minutes at pH 6.8, 86% of the API was released. After 165 minutes at pH 6.8, 96% of the API was released. After 195 minutes at pH 6.8, 98% of the API was released.

The enteric coated tablet demonstrated satisfactory gastric resistance and met the proposed preliminary specification of not less than 75% release in 45 minutes for enteric dosage forms.

Manufacturing Example 2

Table 15 below provides the composition of an enteric coated tablet comprising 2.5 mg of sodium meta-arsenite as the active pharmaceutical ingredient (API). The enteric coated tablet was prepared using the method described below.

TABLE 15

Composition of the enteric coated tablet of Manufacturing Example 2

| Materials | Function | mg/tablet | % w/w |
|---|---|---|---|
| Sodium meta-arsenite (SMA) | API | 2.50 | 1.67 |
| Dibasic calcium phosphate anhydrous, USP (powdered grade) | diluent, filler | 37.50 | 25.00 |
| Silicified microcrystalline cellulose (Prosolv HD90) | filler, compressible diluent | 107.00 | 71.33 |
| Sodium starch glycolate (Explotab) | super disintegrant | 1.50 | 1.00 |
| Colloidal silicon dioxide (Cab-o-sil) | glidant | 0.75 | 0.50 |
| Sodium stearyl fumarate (PRUV) | lubricant | 0.75 | 0.50 |
| Total - core: | | 150.00 | 100 |
| Acryl-EZE Green (93O11863) enteric polymer coating | Enteric coating | 16.50 | |
| Total - as a coated tablet: | | 166.50 | |

In general, and as described in detail below, the sodium meta-arsenite ("SMA") and excipients were blended together (a two-stage blending process without the use of water or solvent) to form a powder blend. The powder blend was then compressed to form the solid core of the tablet. The solid core of the tablet was then coated with an enteric coating.

Blending

The blending process described below was used for blending the ingredients.

The API and the other ingredients for the composition were dispensed and weighed. Since the concentration of the API was very low, a two-stage blending process (utilising an "API premix" and a "main mix") was utilised in an effort to improve blend uniformity.

The API was screened through a 106 µm sieve (the sieving time was about 5 to 8 minutes).

A portion of the calcium phosphate dibasic was added to the sieved API, and the resulting mixture was blended for 30 minutes to provide the "API premix".

The API premix was then blended with the remaining calcium phosphate dibasic and the other excipients (silicified microcrystalline cellulose, sodium starch glycolate, colloidal silicon dioxide, and sodium stearyl fumarate), to provide the "main mix". The main mix was blended with an intensifier bar for 4 minutes to provide a powder blend.

Compressing

The powder blend was compressed on a Key International tablet machine using using 0.25 inch tooling to a target tablet weight of 150 mg±5% (range 142.5-157.5 mg). The solid cores were de-dusted.

The final solid cores demonstrated no significant friability (0.00%) and the hardness was 156.9 N (16 kp).

Enteric Coating

A 25% w/w solid content enteric coating dispersion was prepared by dispersing Acryl-EZE green powder in deionised water. The dispersion was stirred for about 30 minutes (until homogenous).

The de-dusted solid cores were spray-coated (350 g/min) with the dispersion with a weight gain of about 10 to 12% w/w. The pan speed was about 6-8 rpm. The coated tablets were dried after coating.

It is to be understood that, if any prior art publication is referred to herein, such reference does not constitute an admission that the publication forms a part of the common general knowledge in the art, in Australia or any other country.

In the claims which follow and in the preceding description of the invention, except where the context requires otherwise due to express language or necessary implication, the word "comprise" or variations such as "comprises" or "comprising" is used in an inclusive sense, i.e. to specify the presence of the stated features but not to preclude the presence or addition of further features in various embodiments of the invention.

The invention claimed is:

1. A pharmaceutical composition suitable for oral administration comprising:
(a) a solid core comprising sodium meta-arsenite or potassium meta-arsenite, wherein the amount of sodium meta-arsenite or potassium meta-arsenite in the solid core is from about 0.1 to 5.0% w/w of the solid core, and the following pharmaceutically acceptable excipients:
(i) a filler or diluent in a range of from about 5 to 95% w/w of the solid core, wherein the filler or diluent is selected from dibasic calcium phosphate anhydrous, partially pregelatinised starch, silicified microcrystalline cellulose, or a mixture thereof;

(ii) a disintegrant in a range of from about 10 to 90% w/w of the solid core, wherein the disintegrant is selected from L-hydroxypropyl cellulose, partially pregelatinised starch, and sodium starch glycolate;

(iii) a glidant in a range of from about 0.1 to 5% w/w of the solid core, wherein the glidant is colloidal silicon dioxide;

(iv) a lubricant in a range of from about 0.1 to 5% w/w of the solid core, wherein the lubricant is sodium stearyl fumarate; and (v) a binder in a range of up to about 30% w/w of the solid core; wherein the binder is selected from silicified microcrystalline cellulose, partially pregelatinised starch, L-hydroxypropyl cellulose (low substituted hydroxypropylcellulose), and hydroxypropyl cellulose;

and (b) an enteric coating comprising an enteric polymer, wherein the enteric polymer is selected from:
copolymers of two or more of acrylic acids, esters of acrylic acids, methacrylic acids, or esters of methacrylic acids;
cellulose acetate phthalate polymers;
hydroxypropyl methylcellulose phthalate polymers;
hydroxypropyl methylcellulose acetate succinate;
polyvinyl acetate phthalate;
cellulose acetate trimellitate; and
combinations thereof;

wherein the pharmaceutically acceptable excipients are selected such that oxidation of meta-arsenite to meta-arsenate is minimised, wherein the enteric coating provides a weight gain of from about 9.5% w/w of the solid core to a weight gain of about 14% w/w of the solid core, wherein the coating thickness is from about 6.5% to about 15% of the thickness of the pharmaceutical composition, and wherein the pharmaceutical composition is in the form of an enteric coated tablet; and wherein the solid core is selected from the following:

(A) a solid core comprising: (i) sodium meta-arsenite or potassium meta-arsenite, and (ii) the following pharmaceutically acceptable excipients: dibasic calcium phosphate anhydrous, L-hydroxypropyl cellulose, hydroxypropyl cellulose, colloidal silicon dioxide, and sodium stearyl fumarate;

(B) a solid core comprising: (i) sodium meta-arsenite or potassium meta-arsenite, and (ii) the following pharmaceutically acceptable excipients: dibasic calcium phosphate anhydrous powder, dibasic calcium phosphate anhydrous granules, L-hydroxypropyl cellulose, sodium starch glycolate, colloidal silicon dioxide, and sodium stearyl fumarate;

(C) a solid core comprising: (i) sodium meta-arsenite or potassium meta-arsenite, and (ii) the following pharmaceutically acceptable excipients: dibasic calcium phosphate anhydrous, L-hydroxypropyl cellulose, sodium starch glycolate, colloidal silicon dioxide, and sodium stearyl fumarate; and (D) a solid core comprising: (i) sodium meta-arsenite or potassium meta-arsenite, and (ii) the following pharmaceutically acceptable excipients: dibasic calcium phosphate anhydrous, silicified microcrystalline cellulose, sodium starch glycolate, colloidal silicon dioxide, and sodium stearyl fumarate.

2. The pharmaceutical composition according to claim 1, wherein the amount of sodium meta-arsenite or potassium meta-arsenite in the solid core is from about 0.5 to 3.0% w/w of the solid core.

3. The pharmaceutical composition according to claim 1, wherein the solid core comprises sodium meta-arsenite.

4. The pharmaceutical composition according to claim 1, wherein the filler or diluent is present in the solid core of the pharmaceutical composition in an amount of from about 10 to 90% w/w of the solid core.

5. The pharmaceutical composition according to claim 1, wherein the disintegrant is present in the solid core of the pharmaceutical composition in an amount of from about 10 to 50% w/w of the solid core.

6. The pharmaceutical composition according to claim 1, wherein the glidant is present in the solid core of the pharmaceutical composition in an amount of from about 0.3 to 4.0% w/w of the solid core.

7. The pharmaceutical composition according to claim 1, wherein the lubricant is present in the solid core of the pharmaceutical composition in an amount of from about 0.3 to 4.0% w/w of the solid core.

8. The pharmaceutical composition according to claim 1, wherein the binder is present in the solid core of the pharmaceutical composition in an amount of from about 1 to 30% w/w of the solid core.

9. The pharmaceutical composition according to claim 1, wherein the enteric coating provides a weight gain of from about 10% w/w of the solid core to a weight gain of about 14% w/w of the solid core.

10. The pharmaceutical composition according to claim 1, wherein the enteric coating comprises an enteric polymer selected from:
copolymers of two or more of acrylic acids, esters of acrylic acids, methacrylic acids, or esters of methacrylic acids;
cellulose acetate phthalate polymers;
hydroxypropyl methylcellulose phthalate polymers;
hydroxypropyl methylcellulose acetate succinate;
cellulose acetate trimellitate; and
combinations thereof.

11. The pharmaceutical composition according to claim 10, wherein the enteric coating comprises an enteric polymer which is a copolymer of methacrylic acid and ethyl acrylate (1:1).

12. The pharmaceutical composition according to claim 1, wherein the solid core is selected from:

(A') a solid core comprising sodium meta-arsenite, dibasic calcium phosphate anhydrous, L-hydroxypropyl cellulose, hydroxypropyl cellulose, colloidal silicon dioxide, and sodium stearyl fumarate;

(B') a solid core comprising sodium meta-arsenite, dibasic calcium phosphate anhydrous powder, dibasic calcium phosphate anhydrous granules, L-hydroxypropyl cellulose, sodium starch glycolate, colloidal silicon dioxide, and sodium stearyl fumarate;

(C') a solid core comprising sodium meta-arsenite, dibasic calcium phosphate anhydrous, L-hydroxypropyl cellulose, sodium starch glycolate, colloidal silicon dioxide, and sodium stearyl fumarate; and (D') a solid core comprising sodium meta-arsenite, dibasic calcium phosphate anhydrous, silicified microcrystalline cellulose, sodium starch glycolate, colloidal silicon dioxide, and sodium stearyl fumarate.

13. The pharmaceutical composition according to claim 1, wherein the pharmaceutical composition is an enteric coated tablet comprising 1.67% w/w sodium meta-arsenite of the solid core, and having a solid core diameter of about 6.5 mm, a solid core mass of 150 mg, and an enteric coating which has added about 12% w/w of the solid core.

14. A method of manufacturing the pharmaceutical composition according to claim 1, the method comprising the following steps:
   (a) blending an active pharmaceutical ingredient (API) selected from sodium meta-arsenite and potassium meta-arsenite with the following pharmaceutically acceptable excipients to form a powder blend for forming a solid core, wherein the amount of sodium meta-arsenite or potassium meta-arsenite in the solid core is from 0.1 to 5.0% w/w of the solid core:
      (i) a filler or diluent in a range of from about 5 to 95% w/w of the solid core, wherein the filler or diluent is selected from dibasic calcium phosphate anhydrous, partially pregelatinised starch, silicified microcrystalline cellulose, or a mixture thereof,
      (ii) a disintegrant in a range of from about 10 to 90% w/w of the solid core, wherein the disintegrant is selected from L-hydroxypropyl cellulose, partially pregelatinised starch, and sodium starch glycolate,
      (iii) a glidant in a range of from about 0.1 to 5% w/w of the solid core, wherein the glidant is colloidal silicon dioxide,
      (iv) a lubricant in a range of from about 0.1 to 5% w/w of the solid core, and wherein the lubricant is sodium stearyl fumarate, and
      (v) a binder in a range of up to about 30% w/w of the solid core; wherein the binder is selected from silicified microcrystalline cellulose, partially pregelatinised starch, L-hydroxypropyl cellulose (low substituted hydroxypropylcellulose), and hydroxypropyl cellulose;
   (b) compressing the powder blend formed in step (a) to form the solid core; and
   (c) coating the solid core with an enteric coating comprising an enteric polymer, wherein the enteric polymer is selected from:
      copolymers of two or more of acrylic acids, esters of acrylic acids, methacrylic acids, or esters of methacrylic acids;
      cellulose acetate phthalate polymers;
      hydroxypropyl methylcellulose phthalate polymers;
      hydroxypropyl methylcellulose acetate succinate;
      polyvinyl acetate phthalate;
      cellulose acetate trimellitate; and
      combinations thereof;
   wherein the pharmaceutically acceptable excipients are selected such that oxidation of meta-arsenite to meta-arsenate is minimised,
   wherein the enteric coating provides a weight gain of from about 9.5% w/w of the solid core to a weight gain of about 14% w/w of the solid core,
   wherein the coating thickness is from about 6.5% to about 15% of the thickness of the pharmaceutical composition, and
   wherein the pharmaceutical composition is in the form of an enteric coated tablet.

15. A method according to claim 14, wherein step (a) comprises two steps:
   (i) blending the API with a portion of the filler to form an API premix; and
   (ii) blending the glidant, the disintegrant, the lubricant, and the binder with the API premix.

16. A method according to claim 14, wherein step (a) comprises three steps:
   (i) blending the API with a portion of the filler to form an API premix;
   (ii) blending the glidant, the disintegrant, and the binder with the API premix; and then
   (iii) adding the lubricant (which has optionally been mixed with a portion of the mixture from step (ii)), and then blending.

17. A method according to claim 14, wherein step (a) and/or step (b) do not involve the addition of water or solvent.

18. A method for the treatment of a disease or condition in a subject, comprising orally administering to the subject a pharmaceutical composition according to claim 1, wherein the disease or condition is selected from solid malignancy, bone metastasis, metastatic neoplastic disease, primary or metastatic lung tumour, urogenital cancers, leukemia, pain, blood cancers, metastatic cancers, cancer pain, chronic pain, inflammation, autoimmune disorders, immunological disorders, diabetic retinopathy, diabetic vasculopathy, diabetic neuralgia, symptoms associated with insulitis, and ulcerative colitis.

19. The pharmaceutical composition of according to claim 12, wherein the dibasic calcium phosphate anhydrous is about 25% w/w to 80% w/w of the solid core.

20. The pharmaceutical composition of claim 12, wherein the enteric coating comprises an enteric polymer which is a copolymer of two or more of acrylic acids, esters of acrylic acids, methacrylic acids, or esters of methacrylic acids.

21. The pharmaceutical composition of claim 12, wherein the enteric coating comprises an enteric polymer which is a copolymer of two or more of acrylic acids, esters of acrylic acids, methacrylic acids, or esters of methacrylic acids; and
   the enteric coating provides a weight gain of from about 10% w/w of the solid core to a weight gain of about 12% w/w of the solid core.

22. The pharmaceutical composition of claim 12, wherein the enteric coating provides a weight gain of from about 10% w/w of the solid core to a weight gain of about 12% w/w of the solid core.

23. The pharmaceutical composition of claim 12, wherein the dibasic calcium phosphate anhydrous is about 45% w/w to about 80% w/w of the solid core.

24. The pharmaceutical composition of claim 20, wherein the solid core is (A'), (B') or (C').

25. The pharmaceutical composition of claim 21, wherein the solid core is (A'), (B') or (C').

26. The pharmaceutical composition of claim 22, wherein the solid core is (A'), (B') or (C').

27. The pharmaceutical composition of claim 23, wherein the solid core is (A'), (B') or (C').

* * * * *